(12) United States Patent
Evard et al.

(10) Patent No.: US 8,951,225 B2
(45) Date of Patent: Feb. 10, 2015

(54) CATHETERS WITH NON-REMOVABLE GUIDE MEMBERS USEABLE FOR TREATMENT OF SINUSITIS

(75) Inventors: Philip Evard, Los Altos, CA (US);
Ketan P. Muni, San Jose, CA (US);
John Morriss, Portola Valley, CA (US);
John Chang, Mountain View, CA (US)

(73) Assignee: Acclarent, Inc., Menlo Park, CA (US)

( * ) Notice: Subject to any disclaimer, the term of this patent is extended or adjusted under 35 U.S.C. 154(b) by 1803 days.

(21) Appl. No.: 11/438,090

(22) Filed: May 18, 2006

(65) Prior Publication Data
US 2007/0208301 A1 Sep. 6, 2007

Related U.S. Application Data

(63) Continuation-in-part of application No. 11/150,847, filed on Jun. 10, 2005, now Pat. No. 7,803,150, and a continuation-in-part of application No. 11/193,020, filed on Jul. 29, 2005.

(51) Int. Cl.
*A61M 29/00* (2006.01)
*A61M 25/10* (2013.01)
(Continued)

(52) U.S. Cl.
CPC .............. *A61M 25/10* (2013.01); *A61M 29/02* (2013.01); *A61B 17/24* (2013.01); *A61M 2025/1075* (2013.01); *A61M 2025/1079* (2013.01);
(Continued)

(58) Field of Classification Search
USPC ............... 604/96.01, 101.01, 101.02–102.02, 604/508, 514, 915, 919; 606/191–194
See application file for complete search history.

(56) References Cited

U.S. PATENT DOCUMENTS

| 446,173 A | 2/1891 | Hancock |
| 504,424 A | 9/1893 | De Pezzer |
| 513,667 A | 1/1894 | Buckingham |

(Continued)

FOREIGN PATENT DOCUMENTS

| CA | 2013323 | 9/1990 |
| CH | 668188 | 12/1988 |

(Continued)

OTHER PUBLICATIONS

Göttman, et al.; Balloon Dilation of Recurrent Ostial Occlusion of the frontal sinus; Abstract No. B-04353, European Congress of Radiology, Mar. 2001.

(Continued)

*Primary Examiner* — Manuel Mendez
(74) *Attorney, Agent, or Firm* — Frost Brown Todd LLC

(57) ABSTRACT

Balloon catheter, guide catheter and method for dilating openings in paranasal sinuses. A non-removable guide member (e.g., guidewire) extends from the distal end of the balloon catheter. The non-removable guide member initially passes through the opening of the paranasal sinus and is followed by the catheter body on which the balloon is mounted. The balloon is then inflated causing dilation of the opening of the paranasal sinus. In some embodiments, the non-removable guide member may be shapeable so that the operator may place the non-removable guide member in a desired shape prior to insertion of the balloon catheter. In some embodiments, the length of the non-removable guide member may be adjustable such that the operator may adjust the length of the non-removable guide member prior to insertion of the balloon catheter.

60 Claims, 15 Drawing Sheets

(51) Int. Cl.
*A61M 29/02* (2006.01)
*A61B 17/24* (2006.01)

(52) U.S. Cl.
CPC .................. *A61M2025/1093* (2013.01); *A61M 2210/0618* (2013.01)
USPC ...................................................... 604/96.01

(56) References Cited

U.S. PATENT DOCUMENTS

| | | |
|---|---|---|
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,878,671 A | 9/1931 | Cantor |
| 1,828,986 A | 10/1931 | Stevens |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A * | 7/1990 | Hampton et al. ............. 600/585 |
| 4,943,275 A | 7/1990 | Stricker |
| 4,946,466 A | 8/1990 | Pinchuk et al. |
| 4,961,433 A | 10/1990 | Christian |
| 4,966,163 A * | 10/1990 | Kraus et al. .................. 600/585 |
| 4,984,581 A | 1/1991 | Stice |
| 4,994,033 A | 2/1991 | Shockey et al. |
| 4,998,916 A | 3/1991 | Hammerslag et al. |

(56) References Cited

U.S. PATENT DOCUMENTS

| | | | |
|---|---|---|---|
| 4,998,917 A * | 3/1991 | Gaiser et al. | 604/103.13 |
| 5,001,825 A | 3/1991 | Halpern | |
| 5,002,322 A | 3/1991 | Fukumoto | |
| 5,009,655 A | 4/1991 | Daignault, Jr. et al. | |
| 5,019,075 A | 5/1991 | Spears et al. | |
| 5,019,372 A | 5/1991 | Folkman et al. | |
| 5,020,514 A | 6/1991 | Heckele | |
| 5,021,043 A | 6/1991 | Becker et al. | |
| 5,024,650 A | 6/1991 | Hagiwara et al. | |
| 5,024,658 A | 6/1991 | Kozlov et al. | |
| 5,026,384 A | 6/1991 | Farr et al. | |
| 5,030,227 A | 7/1991 | Rosenbluth et al. | |
| 5,041,089 A * | 8/1991 | Mueller et al. | 604/103.09 |
| 5,044,678 A | 9/1991 | Detweiler | |
| 5,053,007 A | 10/1991 | Euteneuer | |
| 5,055,051 A | 10/1991 | Duncan | |
| 5,060,660 A | 10/1991 | Gambale et al. | |
| 5,067,489 A | 11/1991 | Lind | |
| 5,069,226 A | 12/1991 | Yamauchi et al. | |
| 5,087,244 A | 2/1992 | Wolinsky et al. | |
| 5,087,246 A | 2/1992 | Smith | |
| 5,090,595 A | 2/1992 | Vandoninck | |
| 5,090,910 A | 2/1992 | Narlo | |
| 5,102,402 A | 4/1992 | Dror et al. | |
| 5,112,228 A | 5/1992 | Zouras | |
| 5,116,311 A | 5/1992 | Lofstedt | |
| 5,127,393 A | 7/1992 | McFarlin et al. | |
| 5,137,517 A | 8/1992 | Loney et al. | |
| 5,139,510 A | 8/1992 | Goldsmith, III et al. | |
| 5,139,832 A | 8/1992 | Hayashi et al. | |
| D329,496 S | 9/1992 | Wotton | |
| 5,152,747 A | 10/1992 | Olivier | |
| 5,156,595 A | 10/1992 | Adams | |
| 5,163,989 A | 11/1992 | Campbell et al. | |
| 5,167,220 A | 12/1992 | Brown | |
| 5,168,864 A | 12/1992 | Shockey | |
| 5,169,043 A | 12/1992 | Catania | |
| 5,169,386 A | 12/1992 | Becker et al. | |
| 5,171,233 A | 12/1992 | Amplatz et al. | |
| 5,180,368 A | 1/1993 | Garrison | |
| 5,183,470 A | 2/1993 | Wettermann | |
| 5,189,110 A | 2/1993 | Ikematu et al. | |
| 5,195,168 A | 3/1993 | Yong | |
| 5,197,457 A | 3/1993 | Adair | |
| 5,207,695 A | 5/1993 | Trout, III | |
| 5,211,952 A | 5/1993 | Spicer et al. | |
| 5,215,105 A | 6/1993 | Kizelshteyn et al. | |
| 5,221,260 A | 6/1993 | Burns et al. | |
| 5,226,302 A | 7/1993 | Anderson | |
| 5,230,348 A | 7/1993 | Ishibe et al. | |
| 5,236,422 A | 8/1993 | Eplett, Jr. | |
| 5,238,004 A | 8/1993 | Sahatjian et al. | |
| 5,243,996 A | 9/1993 | Hall | |
| D340,111 S | 10/1993 | Yoshikawa | |
| 5,250,059 A | 10/1993 | Andreas et al. | |
| 5,251,092 A | 10/1993 | Brady et al. | |
| 5,252,183 A | 10/1993 | Shaban et al. | |
| 5,255,679 A | 10/1993 | Imran | |
| 5,256,144 A | 10/1993 | Kraus et al. | |
| 5,263,926 A | 11/1993 | Wilk | |
| 5,264,260 A | 11/1993 | Saab | |
| 5,267,965 A | 12/1993 | Deniega | |
| 5,269,752 A | 12/1993 | Bennett | |
| 5,270,086 A | 12/1993 | Hamlin | |
| 5,273,052 A * | 12/1993 | Kraus et al. | 600/585 |
| 5,275,593 A | 1/1994 | Easley et al. | |
| 5,286,254 A | 2/1994 | Shapland et al. | |
| 5,290,310 A | 3/1994 | Makower et al. | |
| 5,295,694 A | 3/1994 | Levin | |
| 5,300,085 A | 4/1994 | Yock | |
| 5,304,123 A | 4/1994 | Atala et al. | |
| 5,308,326 A | 5/1994 | Zimmon | |
| 5,312,430 A | 5/1994 | Rosenbluth et al. | |
| 5,313,967 A | 5/1994 | Lieber et al. | |
| 5,314,408 A | 5/1994 | Salmon et al. | |
| 5,314,417 A | 5/1994 | Stephens et al. | |
| 5,315,618 A | 5/1994 | Yoshida | |
| 5,318,528 A | 6/1994 | Heaven et al. | |
| 5,324,306 A | 6/1994 | Makower et al. | |
| 5,333,620 A | 8/1994 | Moutafis et al. | |
| 5,334,167 A | 8/1994 | Cocanower | |
| 5,334,187 A | 8/1994 | Fischell et al. | |
| 5,335,671 A | 8/1994 | Clement | |
| 5,336,163 A | 8/1994 | DeMane et al. | |
| 5,341,818 A | 8/1994 | Abrams et al. | |
| 5,342,296 A | 8/1994 | Persson et al. | |
| 5,343,865 A | 9/1994 | Gardineer et al. | |
| 5,345,945 A | 9/1994 | Hodgson et al. | |
| 5,346,075 A | 9/1994 | Nichols et al. | |
| 5,346,508 A | 9/1994 | Hastings | |
| 5,348,537 A | 9/1994 | Wiesner et al. | |
| 5,350,396 A | 9/1994 | Eliachar | |
| 5,356,418 A | 10/1994 | Shturman | |
| 5,368,049 A | 11/1994 | Raman et al. | |
| 5,368,558 A | 11/1994 | Nita | |
| 5,368,566 A | 11/1994 | Crocker | |
| 5,372,138 A | 12/1994 | Crowley et al. | |
| 5,372,584 A | 12/1994 | Zink et al. | |
| D355,031 S | 1/1995 | Yoshikawa | |
| 5,386,817 A | 2/1995 | Jones | |
| 5,391,147 A | 2/1995 | Imran et al. | |
| 5,391,179 A | 2/1995 | Mezzoli | |
| 5,402,799 A | 4/1995 | Colon et al. | |
| 5,409,444 A | 4/1995 | Kensey | |
| 5,411,475 A | 5/1995 | Atala et al. | |
| 5,411,476 A | 5/1995 | Abrams et al. | |
| 5,411,477 A | 5/1995 | Saab | |
| 5,415,633 A | 5/1995 | Lazarus | |
| 5,425,370 A | 6/1995 | Vilkomerson | |
| 5,439,446 A | 8/1995 | Barry | |
| 5,441,494 A | 8/1995 | Ortiz | |
| 5,441,497 A | 8/1995 | Narciso, Jr. | |
| 5,445,646 A | 8/1995 | Euteneuer et al. | |
| 5,450,853 A | 9/1995 | Hastings et al. | |
| 5,451,221 A | 9/1995 | Cho et al. | |
| 5,454,817 A | 10/1995 | Katz | |
| 5,458,572 A * | 10/1995 | Campbell et al. | 604/103.08 |
| 5,459,700 A | 10/1995 | Jacobs | |
| 5,465,717 A | 11/1995 | Imran et al. | |
| 5,465,733 A | 11/1995 | Hinohara et al. | |
| 5,478,565 A | 12/1995 | Geria | |
| 5,486,181 A | 1/1996 | Cohen et al. | |
| 5,496,338 A | 3/1996 | Miyagi et al. | |
| 5,497,783 A | 3/1996 | Urick et al. | |
| 5,507,301 A | 4/1996 | Wasicek et al. | |
| 5,507,725 A | 4/1996 | Savage et al. | |
| 5,507,766 A | 4/1996 | Kugo et al. | |
| 5,507,795 A | 4/1996 | Chiang et al. | |
| 5,512,055 A | 4/1996 | Domb et al. | |
| 5,514,128 A | 5/1996 | Hillsman et al. | |
| 5,519,532 A | 5/1996 | Broome | |
| 5,531,676 A | 7/1996 | Edwards et al. | |
| 5,533,985 A | 7/1996 | Wang | |
| 5,538,008 A | 7/1996 | Crowe | |
| 5,546,964 A | 8/1996 | Stangerup | |
| 5,549,542 A | 8/1996 | Kovalcheck | |
| 5,558,073 A | 9/1996 | Pomeranz et al. | |
| 5,558,652 A | 9/1996 | Henke | |
| 5,562,619 A | 10/1996 | Mirarchi et al. | |
| 5,568,809 A | 10/1996 | Ben-Haim | |
| 5,571,086 A | 11/1996 | Kaplan et al. | |
| 5,578,007 A | 11/1996 | Imran | |
| 5,578,048 A | 11/1996 | Pasqualucci et al. | |
| 5,582,575 A | 12/1996 | Heckele | |
| 5,584,827 A | 12/1996 | Korteweg et al. | |
| 5,591,194 A | 1/1997 | Berthiaume | |
| 5,599,284 A | 2/1997 | Shea | |
| 5,599,304 A | 2/1997 | Shaari | |
| 5,599,576 A | 2/1997 | Opolski | |
| 5,601,087 A | 2/1997 | Gunderson et al. | |
| 5,601,594 A | 2/1997 | Best | |
| 5,607,386 A | 3/1997 | Flam | |
| 5,617,870 A | 4/1997 | Hastings et al. | |
| 5,626,374 A | 5/1997 | Kim | |

(56) References Cited

U.S. PATENT DOCUMENTS

| | | |
|---|---|---|
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim et al. |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |

(56) References Cited

U.S. PATENT DOCUMENTS

| | | |
|---|---|---|
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,596,009 B1 | 7/2003 | Jelic |
| 6,607,546 B1 | 8/2003 | Murken |
| 6,610,059 B1 | 8/2003 | West, Jr. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,176 B2 | 2/2006 | Lau |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |

(56) References Cited

U.S. PATENT DOCUMENTS

| | | | |
|---|---|---|---|
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,347,868 B2 | 3/2008 | Burnett et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,610,104 B2 | 10/2009 | Kaplan et al. |
| 7,618,450 B2 | 11/2009 | Zarowski et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,691,120 B2 | 4/2010 | Shluzas et al. |
| 7,717,933 B2 | 5/2010 | Becker |
| 7,736,301 B1 | 6/2010 | Webler et al. |
| 7,740,642 B2 | 6/2010 | Becker |
| 7,753,929 B2 | 7/2010 | Becker |
| 7,785,315 B1 | 8/2010 | Muni et al. |
| 7,799,048 B2 | 9/2010 | Hudson et al. |
| 7,799,337 B2 | 9/2010 | Levin |
| 7,833,282 B2 | 11/2010 | Mandpe |
| 7,837,672 B2 | 11/2010 | Intoccia |
| D630,321 S | 1/2011 | Hamilton, Jr. |
| D632,791 S | 2/2011 | Murner |
| 7,881,769 B2 | 2/2011 | Sobe |
| 7,988,705 B2 | 8/2011 | Galdonik et al. |
| 8,014,849 B2 | 9/2011 | Peckham |
| 8,088,101 B2 | 1/2012 | Chang et al. |
| 8,146,400 B2 | 4/2012 | Goldfarb et al. |
| 8,147,545 B2 | 4/2012 | Avior |
| 8,172,828 B2 | 5/2012 | Chang et al. |
| 8,197,433 B2 | 6/2012 | Cohen |
| 8,197,552 B2 | 6/2012 | Mandpe |
| 8,249,700 B2 | 8/2012 | Clifford et al. |
| 8,414,473 B2 | 4/2013 | Jenkins et al. |
| 8,425,457 B2 | 4/2013 | John et al. |
| 2001/0004644 A1 | 6/2001 | Levin |
| 2001/0005785 A1 | 6/2001 | Sachse |
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 | 10/2001 | Malackowski et al. |
| 2001/0051761 A1 | 12/2001 | Khadem |
| 2002/0002349 A1 | 1/2002 | Flaherty et al. |
| 2002/0006961 A1 | 1/2002 | Katz et al. |
| 2002/0010384 A1 | 1/2002 | Shahidi et al. |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0055746 A1 | 5/2002 | Burke et al. |
| 2002/0062133 A1 | 5/2002 | Gilson et al. |
| 2002/0077593 A1 | 6/2002 | Perkins et al. |
| 2002/0077852 A1 | 6/2002 | Ford et al. |
| 2002/0082558 A1 | 6/2002 | Samson et al. |
| 2002/0082583 A1 | 6/2002 | Lerner |
| 2002/0090388 A1 | 7/2002 | Humes et al. |
| 2002/0103459 A1 | 8/2002 | Sparks et al. |
| 2002/0107475 A1 | 8/2002 | Maginot |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014036 A1 | 1/2003 | Varner et al. |
| 2003/0017111 A1 | 1/2003 | Rabito |
| 2003/0018291 A1 | 1/2003 | Hill et al. |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073900 A1 | 4/2003 | Senarith et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0109810 A1 | 6/2003 | Brennan et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0171650 A1 | 9/2003 | Tartaglia et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0209096 A1 | 11/2003 | Pandey et al. |
| 2003/0220551 A1 | 11/2003 | Kimball et al. |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1* | 4/2004 | Becker ............... 606/196 |
| 2004/0097788 A1 | 5/2004 | Mourlas et al. |
| 2004/0098017 A1 | 5/2004 | Saab et al. |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |

(56) References Cited

U.S. PATENT DOCUMENTS

| | | |
|---|---|---|
| 2004/0181175 A1 | 9/2004 | Clayman et al. |
| 2004/0193073 A1 | 9/2004 | DeMello et al. |
| 2004/0193139 A1 | 9/2004 | Armstrong et al. |
| 2004/0220516 A1 | 11/2004 | Solomon et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027249 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco et al. |
| 2005/0059930 A1 | 3/2005 | Garrison et al. |
| 2005/0059931 A1 | 3/2005 | Garrison et al. |
| 2005/0089670 A1 | 4/2005 | Large et al. |
| 2005/0107720 A1 | 5/2005 | Burmeister et al. |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228260 A1 | 10/2005 | Burwell et al. |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1 | 1/2006 | Chang et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0173291 A1 | 8/2006 | Glossop |
| 2006/0173382 A1 | 8/2006 | Schreiner |
| 2006/0189844 A1 | 8/2006 | Tien |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott et al. |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0250105 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0154345 A1 | 6/2008 | Taylor |
| 2008/0172033 A1 | 7/2008 | Keith et al. |
| 2008/0187098 A1 | 8/2008 | Gertner et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088728 A1 | 4/2009 | Dollar et al. |
| 2009/0093823 A1 | 4/2009 | Chang et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0192492 A1 | 7/2009 | Eaton et al. |
| 2009/0198216 A1 | 8/2009 | Muni et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0121308 A1 | 5/2010 | Muni et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | John et al. |

(56) References Cited

U.S. PATENT DOCUMENTS

| | | | |
|---|---|---|---|
| 2013/0245608 A1 | 9/2013 | Muni et al. | |
| 2013/0261388 A1 | 10/2013 | Jenkins et al. | |

FOREIGN PATENT DOCUMENTS

| | | |
|---|---|---|
| CN | 2151720 | 1/1994 |
| CN | 2352818 | 12/1999 |
| DE | 03202878 | 8/1983 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0200430 | 11/1986 |
| EP | 0257605 | 3/1988 |
| EP | 0355996 | 2/1990 |
| EP | 0418391 | 3/1991 |
| EP | 0427852 | 5/1991 |
| EP | 0515201 | 1/1992 |
| EP | 0623582 | 11/1994 |
| EP | 0624349 | 11/1994 |
| EP | 744400 | 11/1996 |
| EP | 0744400 | 11/1996 |
| EP | 0585757 | 6/1997 |
| EP | 893426 | 1/1999 |
| EP | 0893426 | 1/1999 |
| EP | 0920882 | 6/1999 |
| EP | 0974936 | 1/2000 |
| EP | 01042998 | 10/2000 |
| EP | 1086664 | 3/2001 |
| EP | 01166710 | 1/2002 |
| EP | 01413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-067935 | 6/1978 |
| JP | 5367935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | 6-277296 | 10/1994 |
| JP | 07-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WF | 99/32041 | 7/1999 |
| WO | 90/11053 | 10/1990 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 94/21320 | 9/1994 |
| WO | WO 95/02430 | 1/1995 |
| WO | WO 96/29071 | 9/1996 |
| WO | 97/24161 | 6/1997 |
| WO | WO 98/55174 | 12/1998 |
| WO | WO 99/00064 | 1/1999 |
| WO | WO 99/24106 | 5/1999 |
| WO | WO 99/26692 | 6/1999 |
| WO | WO 99/30655 | 6/1999 |
| WO | WO 99/59649 | 11/1999 |
| WO | 00/09192 | 2/2000 |
| WO | WO 00/09190 | 2/2000 |
| WO | 00/23009 | 4/2000 |
| WO | 00/51672 | 9/2000 |
| WO | WO 00/53252 | 9/2000 |
| WO | WO 01/05462 | 1/2001 |
| WO | WO 01/45572 | 6/2001 |
| WO | 01/56481 | 8/2001 |
| WO | WO 01/54558 | 8/2001 |
| WO | 01/70325 | 9/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 02/089899 | 11/2002 |
| WO | 03/049603 | 6/2003 |
| WO | 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/035204 | 3/2007 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Göttman, et al., Balloon dilatation of recurrent ostial occlusion of the front sinus; ECR, Mar. 2, 2001.
Göttman, et al., Successful Treatment of Recurrent Post-operative Frontal Sinus Stenoses by Balloon Dilatation; CIRSE, Oct. 5, 2002.
Göttman, et al., Balloon dilatation in the nasal cavity and paranasal sinuses; CIRSE, Sep. 25, 2004.
Robison, J. Mathews, M.D., Pressure Treatment of Purulent Maxillary Sinusitis, Texas State Journal of Medicine, May 1951, pp. 281-288.
Robison, J. Mathews, M.D., Pressure Treatment of Maxillary Sinusitis, J.A.M.A., May 31, 1952, pp. 436-440.
Strohm et al. Die Behandlung von Stenosen der oberen Luftwege mittels röntgenologisch gesteuerter Ballondilation Sep. 25, 1999.
USPTO Office Action dated Oct. 29, 2008 in U.S. Appl. No. 11/347,147, filed Feb. 2, 2006.
USPTO Office Action dated Mar. 3, 2009 in U.S. Appl. No. 12/117,582, filed May 8, 2008.
USPTO Office Action dated Mar. 4, 2009 in U.S. Appl. No. 12/118,931, filed May 12, 2008.
USPTO Office Action dated Oct. 6, 2008 in U.S. Appl. No. 10/259,300, filed Sep. 30, 2002.
USPTO Office Action dated Oct. 9, 2007 in U.S. Appl. No. 10/259,300, filed Sep. 30, 2002.

(56) References Cited

OTHER PUBLICATIONS

USPTO Office Action dated Jul. 7, 2006 in U.S. Appl. No. 10/259,300, filed Sep. 30, 2002.
USPTO Office Action dated Jan. 24, 2008 in U.S. Appl. No. 10/259,300, filed Sep. 30, 2002.
USPTO Office Action dated Feb. 13, 2007 in U.S. Appl. No. 10/259,300, filed Sep. 30, 2002.
USPTO Office Action dated Mar. 17, 2009 in U.S. Appl. No. 11/690,127, filed Mar. 22, 2007.
Argon Medical. Maxxim Medical. Ad for Sniper EliteTM Hydrophilic Ni-Ti Alloy Guidewire (2001).
Aust, R., et al 'The Functional Size of the Human Maxillary Ostium in Vivo' Acta. Otolaryn. (1978) vol. 78 pp. 432-435.
Bairn, D.S., MD *Grossman's Cardiac Catheterization, Angiography, and Intervention* (2000) Lippincott Williams & Wilkins pp. 76, 84 & 214.
Barrett, S. 'Be Wary of Neurocranial Restructuring (NCR)' Chirobase (available at: http://www.chirobase.org/06DD/ncr.html) (Jul. 2003.).
Bartal, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. http://inventors.about.com/library/inventors/blcatheter.htm?p=1.
Benninger et al. Adult Chronic Rhinosinusitis: Definitions, Diagnosis, Epidemiology, and Pathophysiology Arch Otolarygol Head and Neck Surg. (Sep. 2003) vol. 129 pp. S1-S32.
Bent et al. 'The Frontal Cell as a Cause of Frontal Sinus Obstruction' American Journal of Rhinology. (1994) vol. 8, No. 4 pp. 185-191.
Binner et al. 'Fibre-Optic Transillumination of the Sinuses: A Comparison of the Value of Radiography and Transillumination in Antral Disease' Clinical Otolaryngology. (1978) vol. 3 pp. 1-11.
Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Bumm, P., H. Kaiser et al 'Cortizontherapie, Corticoide in Klinik und Praxis' Thieme, Stuggart (1992) pp. 390-401.
Casiano et al. 'Endoscopic Lothrop Procedure: The University of Miami Experience' American Journal of Rhinology (1998) vol. 12, No. 5 pp. 335-339.
Casserly, I.P. et al Chapter 7. 'Guides and Wires in Percutaneous Coronary Intervention' *Strategic Approaches in Coronary Intervention* (2006) Lippincott Williams & Wilkins pp. 91-99.
Chien, Y.W. et al. *Nasal Systemic Drug Delivery, Drugs and the Pharmaceutical Sciences* (1989) Marcel Dekker, Inc. Chapter 3, pp. 39-88.
Cohen et al 'Endoscopic Sinus Surgery: Where we are and where we're going' Current Opinion in Otolaryngology & Head and Neck Surgery (2005) vol. 13 pp. 32-38.
Colla, A. et al 'Trihaloacetylated Enol Ethers—General Synthetic Procedure and Heterocyclic Ring Closure Reactions with Hydroxylamine' Synthesis. (Jun. 1991) pp. 483-486.
Costa, M.N. et al 'Endoscopic Study of the Intranasal Ostium in External Dacryocystorhinostomy Postoperative. Influence of Saline Solution and 5-Flurorouracil' Clinics. (2007) vol. 62, Issue 1 pp. 41-46. http://www.scielo.br/scielo.php?pid=S1807-59322007000100007&script=sci_arttext.
Cussler, E.L. *Diffusion: Mass Transfer in Fluid Systems* Cambridge University Press (1996).
Davis, G.E. et al., 'A Complication From Neurocranial Restructuring' Arch Otolaryngology Head Neck Surg. (Apr. 2003) vol. 129 pp. 472-474.
Deutschmann, R. et al. 'A Contribution to the Topical Treatment of [Maxillary] Sinusitis Preliminary Communication' Stomat DDR 26, (1976) pp. 585-592.

Domb, A. et al *Handbook of Biodegradable Polymers* Harwood Academic Publishers (1997).
Draf, W. 'Endonasal Micro-Endoscopic Frontal Sinus Surgery: the Fulda Concept' Op Tech Otolaryngol Head Neck Surg. (1991) vol. 2 pp. 234-240.
Edmond et al 'ENT Surgical Stimulator' Nov. 1998 Final Report Cooperative Agreement No. DAMD17-95-2-5023.
ENT Checklist; Physical Examination Performance Checklist.
Eremychev, V.A. 'Needles for Puncture and Drainage of the Maxillary Sinus' Meditsinskaya Tekhnika, No. 5 (1974) pp. 54-55.
Feldman, R.L. et al 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Fletcher I.E. 'New Operation and Instruments for Draining the Frontal Sinus' Ann. Otol Rhinol Laryngol. (1905) vol. 14 pp. 515-519.
Ford, C.N. 'A Multipurpose Layngeal Injector Device' Otolaryngol. Head Neck Surg (1990) vol. 103, No. 1 pp. 135-137.
Friedman, M. M.D., et al 'Frontal Sinus Surgery: Endoscopic Technique' Operative Techniques in Otolaryngology—Head and Neck Surgery. (Jun. 2001) vol. 12, No. 2 pp. 60-65.
Friedman, et al 'Intraoperative and Postoperative Assessment of Frontal Sinus Patency by Transillumination' Laryngoscope. (Apr. 2000) vol. 110 pp. 683-684.
Friedman et al 'Middle Turbinate Medialization and Preservation in Endoscopic Surgery' Otolaryngol. Head Neck Surg. (2000) vol. 123, No. 1, Part 1. pp. 76-80.
Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.
Gatot, A. et al., 'Early Treatment of Orbital Floor Fractures with Catheter Balloon in Children' Int. J. Pediatric Otorhinolaryngol (1991) vol. 21 pp. 97-101.
Gerus, I.I. et al 'β-Ethoxyvinyl Polyfluroroalkyl Ketones—Versatile Synthones in Fluoroorganic Chemistry' Journal of Fluorine Chemistry. (1994) vol. 69 pp. 195-198. Elsevier Science S.A.
Good, R.H. 'An Intranasal Method for Opening the Frontal Sinus Establishing the Largest Possible Drainage' Laryngoscope. (1908) vol. 18 pp. 266-274.
Gopferich 'Polymer Degradation and Erosion: Mechanisms and Applications' Eur. J. Pharm. Biophar. (1996) vol. 42 pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.
Gottman, et al. 'Balloon Dilatation in the Nasal Cavity and Paranasal Sinuses' CIRSE. (Sep. 25, 2004) pp. 1-27.
Gottman, et al. 'Balloon Dilatation of Recurrent Ostial Occlusion of the Front Sinus' Abstract No. B-04353. European Congress of Radiology. (Mar. 2, 2001).
Gottman, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of the Association of West German ENT Physicians (1999).
Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.
Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.
Hojo, M. et al 'Electrophilic Substitutions of Olefinic Hydrogens II. Acylation of Vinyl Ethers and N Vinyl Amides' Chemistry Letters (1976) pp. 499-502.
Hopf, J.U.G. et al 'Miniature Endoscopes in Otorhinolaryngologic Applications' Min Invas Ther & Allied Technol (1998) vol. 7, No. 3 pp. 209-218.
Hosemann, W. et al *A Dissection Course on Endoscopic Endonasal Sinus Surgery* (2005) Endo-Press, Tuttlingen pp. 4-37.

(56) References Cited

OTHER PUBLICATIONS

Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.
Hosemann, M.E. et al 'Experimentelle Untersuchungen zur Wundheilung in den Nasennebenholhlen. II. Spontaner Wundschluss und medikamentose Effekte im standardisierten Wundmodell.' HNO 39 (1991) pp. 48-54.
Hosemann W.G. et al *Minimally Invasive Endonasal Sinus Surgery* Thieme, Stuttgart, New York (2000).
Hosemann, M.E. et al 'Normal Wound Healing of the Paranasal Sinuses—Clinical and Experimental Investigations' Eur Arch Otorhinolarygol. (1991) vol. 248 pp. 390-394.
Hosemann, W. et al 'Weiterbehandlung nach Nasennebenhohleneingriffen, Part 2: Theapeutische Maβnahmen' HNO akutell 7 (1999) pp. 291-302.
Hospital Corpsman Sickcall Screener's Handbook. Naval Hospital Great Lakes (Apr. 1999) http://www.brooksidepress.org/Products/Operationa.Medicine/DATA. 2001 pp. 1-6.
Hybels, R.L. 'Transillumination During Osteoplastic Frontal Sinusotomy' The Laryngoscope (Sep. 1981) vol. 91 pp. 1560.
Ijaduola, T.G.A. 'Use of a Foley Catheter for Short-Term Drainage in Frontal Sinus Surgery' The Journal of Laryngology and Otology. (1989) vol. 103 pp. 375-378.
Iro, H. et al 'A New Device for Frontal Sinus Endoscopy: First Clinical Report' Otolaryngol. Head Neck Surg (2001) vol. 125 No. 6 pp. 613-616.
Jacobs, J.B. '100 Years of Frontal Sinus Surgery' Laryngoscope. (1997) vol. 107 pp. 1-36.
Kennedy, D.W., M.D. et al *Diseases of the Sinuses Diagnosis and Management* (Copyright 2001) by B.C. Decker Inc.
Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.
Kingdom, T.T. et al 'Image-Guided Surgery of the Sinuses: Current Technology and Applications' Otolaryngol. Clin. North Am. (Apr. 2004) vol. 37, No. 2 pp. 381-400.
Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.
Kozlov et al 'Diagnosis and Treatment of Sinusitis by YAMIK Sinus Catheters' Rhinology (1996) vol. 34. pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery (1991) vol. 2, No. 4 pp. 226-231.
Laliberte F. et al 'Clinical and Pathologic Methods to Assess the Long-Term Safety or Nasal Corticosteroids' Allergy (2000) vol. 55, No. 8 pp. 718-722.
Lang, E.V. et al 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium. General Session Abstracts. Jul. 21-24, 1993.
Large, G.C. 'Crystalline Tetracycline Hydrochloride in the Treatment of Acute and Chronic Maxillary Sinusitis' Canad. M. A. J. (1958) vol. 79 pp. 15-16.
Lund, V.J. 'Maximal Medical Therapy for Chronic Rhinosinusitis' Otolaryngol Clin N Am. (2005) vol. 38 pp. 1301-1310.
Maran, A.G.D. et al 'The Use of the Foley Catheter in the Tripod Fracture' J. Laryngol. Otol (1971) vol. 85, Issue 9 pp. 897-902.
May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.
Medtronic, xomed.com-MicroFrance Catalog Browser. http://www.xomcat.com/xomfrance/index.php?zone=both&cat=18&sub=58&prodline=1272 (Dec. 31, 2003) pp. 1-2.
Mehan, V.K. et al 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron (2000) vol. 56 pp. 10067-10074. Elseview Science Ltd.
Metson, R. et al 'Endoscopic Treatment of Sphenoid Sinusitis' Otolaryngol. Head Neck Surg (1996) vol. 114, No. 6 pp. 736-744.
Metson, R. 'Holmium: YAG Laser Endoscopic Sinus Surgery: A Randomized Controlled Study' Laryngoscope (Jan. 1996) vol. 106, Issue 1, Supplement 77 pp. 1-18.
Miller et al. 'Management of Fractures of the Supraorbital Rim' Journal of Trauma (Jul. 1978) vol. 18, No. 7 pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.
Mols, B. 'Moveable Tool Tip for Keyhole Surgery' Delft Outlook (2005) vol. 3 pp. 13-17.
Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.
Park, K. et al *Biodegreadable Hydrogels for Medicinal Substance Delivery* (1993) Technomic Publishing Inc. Lancaster.
Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.
Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L. et al 'Balloon Technique for Treatment of Frontal Sinus Fractures' The Journal of Laryngology & Otology (1967), vol. 81. pp. 1157-1161.
Pownell, P.H. et al 'Diagnostic Nasal Endoscopy' Plastic & Reconstructive Surgery (1997) vol. 99, Iss. 5 pp. 1451-1458.
Prince et al 'Analysis of the Intranasal Distribution of Ointment' J Otolaryngol. (1997) vol. 26 pp. 357-360.
Ramsdale, D.R. *Illustrated Coronary Intervention A case-oriented approach* (2001) Martin Dunitz Ltd. pp. 1-5.
Ritter, F.N. et al *Atlas of Paranasal Sinus Surgery* (1991) Igaku-Shoin Medical Pub pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine. (May 1951) pp. 281-288.
Sama, A. et al 'Current Opinions on the Surgical Management of Frontal Sinus Disease' ENT News. www.pinpointmendical.com/ent-news (2009) vol. 17 No. 6 pp. 60-63.
Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.
*Sawbones Catalog* 2001, Pacific Research Laboratories, Inc., Vashon, Washington 98070 USA.
Saxon, R.R., et al 'Technical Aspects of Accessing the Portal Vein During the TIPS Procedure' J. Vase. Interv. Radiol. (1997) vol. 8, No. 5 pp. 733-744.
Schaefer, S.D., M.D. *Rhinology and Sinus Disease A Problem-Oriented Approach* (Copyright 1988) by Mosby, Inc.
Schneider. Pfizer Ad for Softip.
Shah, N.J. et al 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at www.bhj.org/journal/1999_4104_oct99/sp_659.htm.
Single-Pole and Multi-Pole Lightguides for UV Spot Light Curing Systems. http://www.dymax.com/products/curing_equipment/lightguids/light. (2004) pp. 1-2.

(56) References Cited

OTHER PUBLICATIONS

Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.
St. Croix, et al 'Genes Expressed in Human Tumor Endothelium' Science (May 15, 2000) vol. 289 pp. 1197-1202.
Stammberger H. 'Komplikationen entzundlicher Nasen-nebenhohlenerkrankungen eischließlich iatrogen bedingter Komplikationen.' Eur Arch Oti-Rhino-Laryngol Suppl. (Jan. 1993) pp. 61-102.
Stammberger, et al 'Special Endoscopic Anatomy of the Lateral Nasal Wall and Ethmoidal Sinuses' Functional Endoscopic Sinus Surgery. (1991) Ch. 3, pp. 49-87.
Strohm et al Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Au Balloon' Sep. 25, 1999.
Strohm, et al 'Treatment of the Stenoses of the Upper Air Routes by Balloon Dilation' Sudwestdeutscher (Sep. 25, 1999) Abstract 45 pp. 1-3.
SurgTrainer Product Information 'Incisive Human Nasal Model for ESS Training' Surg Trainer, Ltd. Ibaraki, Japan (2004) http://www1.accsnet.ne.jp/~juliy/st/en/partslist.html.
Tabor, M.H. et al 'Symptomatic Bilateral Nasolacrimal Duct Cysts in a Newborn—Rhinoscopic Clinic' Ear, Nost & Throat Journal (2003) http://findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinolaringol. (1978) vol. 6 pp. 45-47.
Terumo. Medi-Tech. Boston Scientific. (1993) Ad for Glidewire.
The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4.
Weber, R. et al 'Endonasale Stirnhohlenchirugie mit Langzeiteinlage eines Platzhalters' Laryngol. Rhinol. Otol. (1997) vol. 76 pp. 728-734. (English Abstract).
Weber, R. et al 'Videoendoscopic Analysis of Nasal Steroid Distribution' Rhinology (1999) vol. 37 pp. 69-73.
Weiner, R.I., D.O. et al 'Development and Application of Transseptal Left Heart Catheterization' Cathet. Cardiovasc. Diagn. (1988) vol. 15, No. 2 pp. 112-120.
Wiatrak, B.J. et al 'Unilateral Choanal Atresia: Initial Presentation and Endoscopic Repair' International Journal of Pediatric Otorhinolaryngology (1998) vol. 46 pp. 27-35.
Woog, et al. 'Paranasal Sinus Endoscopy and Orbital Fracture Repair' Arch Ophthalmol. (May 1998) vol. 116 pp. 688-691.
Wormald, P.J. et al 'The 'Swing-Door' Technique for Uncinectomy in Endoscopic Sinus Surgery' The Journal of Laryngology and Otology (1998) vol. 112 pp. 547-551.
Xomed-Treace. Bristol-Myers Squibb. Ad for Laser Shield II. Setting the Standards for Tomorrow.
Yamauchi, Y. et al 'Development of a Silicone Model for Endoscopic Sinus Surgery' proc International Journal of Computer Assisted Radiology and Surgery (1999) vol. 99 pp. 1039.
Yamauchi, Y. et al 'A Training System for Endoscopic Sinus Surgery with Skill Evaluation' Computer Assisted Radiology and Surgery (2001) with accompanying poster presentation.
Yanagisawa et al 'Anterior and Posterior Fontanelles.' Ear, Nose & Throat Journal (2001) vol. 80. p. 10-12.
Zimarino, M., MD et at 'Initial Experience with the EuropassTM: A New Ultra-Low Profile Monorail Balloon Catheter' Cathet. Cardiovasc. Diagn. (1994) vol. 33, No. 1 pp. 76-79.
http://www.invotec.net/rhinology/ksplint.html. K-Splint Internal Nasal Splints; Jan. 25, 2007.
http://www.doylemedical.com/nasalsplints.htm; Doyle Nasal Splints; Jan. 25, 2007.
http://www.technologyforlife.com.au/ent/nasal.html; Nasal Surgery and Accessories; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
International Preliminary Report on Patentability dated Aug. 25, 2006 from PCT/US05/25371.
International Preliminary Report on Patentability dated Oct. 4, 2007 from PCT/US06/002004.
International Preliminary Report dated Feb. 15, 2008 from PCT/US05/13617.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/0009111.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report dated Nov. 30, 2009 re: PCT/US2009/057203.

(56) References Cited

OTHER PUBLICATIONS

International Search Report from PCT Application No. PCT/US2009/057203 dated Nov. 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.
International Search Report dated Mar. 28, 2011 re: PCT/US2010/061850.
Partial European Search Report dated Sep. 20, 2007 re: 07252018.
Partial European Search Report dated Mar. 25, 2008 re: 07252018.
Supplemental European Search Report dated Jun. 2, 2008 re: EP05773189.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 from 07777004.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/116,118, filed Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/648,159, filed Dec. 29, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/789,705, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.

(56) References Cited

OTHER PUBLICATIONS

USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.
Gottmann, et al. 'Balloon Dilatation of Recurrent Ostial Occlusion of the Frontal Sinus' CIRSE Abstract (Mar. 2001) B-04353.
Gottman, et al., 'Balloon Dilatation of Recurrent Ostial Occlusion of the Front Sinus' OASIS-Online Abstract Submission and Invitation System, 1996-2006, Coe Truman Technologies, Inc.
Ingals, E.F. 'New Operation and Instruments for Draining the Frontal Sinus' Ann. Otol. Rhinol. Layyngol. vol. 14 (1905) pp. 644-649.
Sinusitis, Maxillary, Acute Surgical Treatment. Http://www.emedicine.com/ent/topic340.htm. Aug. 29, 2006. pp. 1-11.
SurgTrainer Product Information 2003, Surg Trainer, Ltd. Ibaraki, Japan.
Australian Office Action, Examiners First Report dated Dec. 9, 2011 for Application No. AU 2006292818.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. Ep 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Supplemental European Search Report dated Mar. 16, 2010 for Application No. EP 06718986.
PCT Search Report dated Nov. 30, 2009 for Application No. UPCT/US2009/057203.
International Preliminary Report on Patentability dated Jun. 29, 2011 for Application No. PCT/US2009/069143.
International Search Report dated Mar. 31, 2011 for Application No. PCT/US2010/060898.
International Search Report dated Mar. 31, 2011 for Application No. PCT/US2009/069143.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Russian Office Action dated Sep. 28, 2012 for Application No. RU 2011130530.
Russian Office Action dated Mar. 19, 2013 for Application No. RU 2011130530.
USPTO Office Action dated Dec. 29, 2008 for U.S. Appl. No. 11/193,020.
USPTO Office Action dated May 13, 2009 for U.S. Appl. No. 11/193,020.
US Non-Provisional U.S. Appl. No. 11/648,158, filed Dec. 29, 2006.
US Non-Provisional U.S. Appl. No. 11/804,308, filed May 16, 2007.
US Non-Provisional U.S. Appl. No. 11/804,309, filed May 16, 2007.
US Non-Provisional U.S. Appl. No. 13/840,430, filed Mar. 15, 2013.
Ingals, E.F. 'New Operation and Instruments for Draining the Frontal Sinus' Ann. Otol Rhinol Laryngol. (1905) vol. 14 pp. 515-519.
European Search Report dated Sep. 27, 2011 re: EP10182961.
International Search Report dated Mar. 31, 2010 re: PCT/US2009/069143.
International Search Report dated Aug. 9, 2011 re: PCT/US2011/038751.
Supplemental European Search Report dated Jul. 1, 2009 re: EP06815285.
Supplemental European Search Report dated Mar. 31, 2011 re: EP05798331.
Supplemental European Search Report dated Aug. 30, 2011 re: EP06800540.
Supplemental European Search Report dated Sep. 29, 2011 re: EP07750248.
Japanese Office Action, Notification of Reasons for Refusal dated Sep. 18, 2013 for Application No. JP 2011-527942.
English Machine Translation for Application No. JP 5-503650.

\* cited by examiner

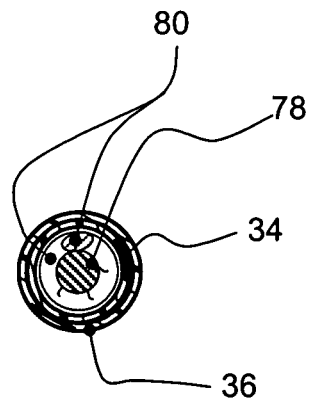
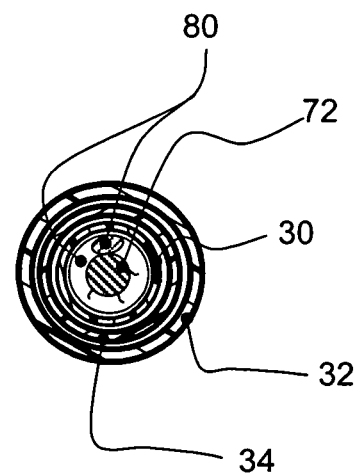
*Fig. 2 A*
*Fig. 2 B*
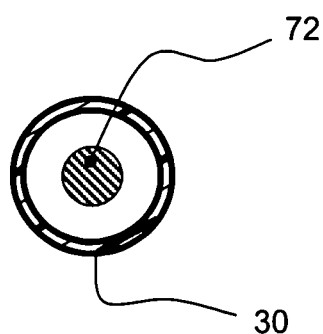
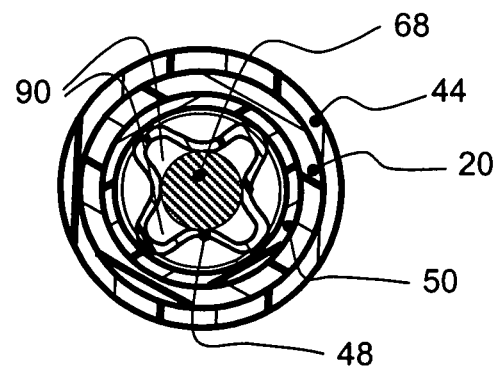
*Fig. 2 C*
*Fig. 2 D*

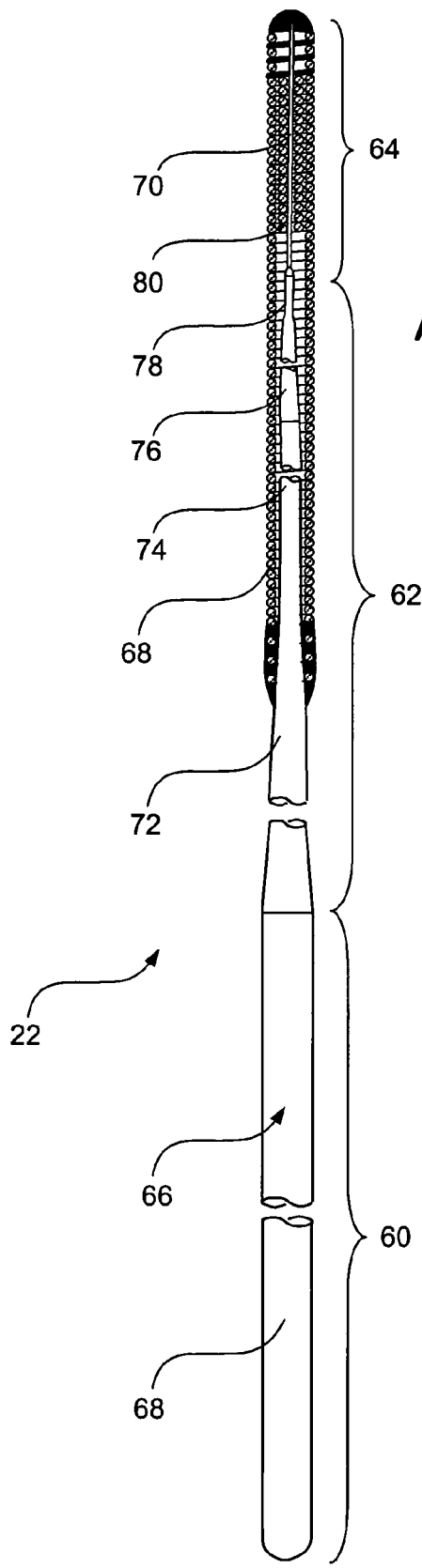
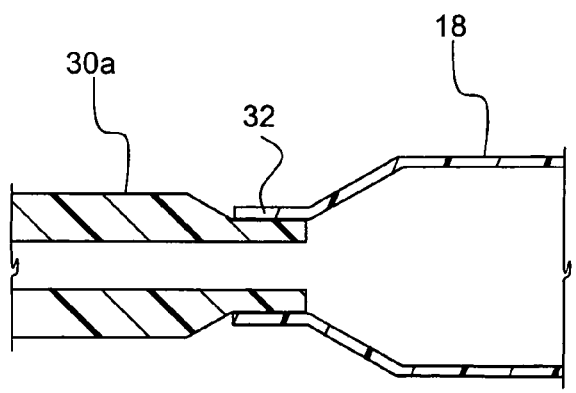

CATHETERS WITH NON-REMOVABLE GUIDE MEMBERS USEABLE FOR TREATMENT OF SINUSITIS

RELATED APPLICATION

This application is a continuation-in-part of U.S. patent application Ser. No. 11/150,847 entitled "Devices, Systems and Methods Useable for Treating Sinusitis" filed Jun. 10, 2005, issued Sep. 9, 2010 as U.S. Pat. No. 7,803,150, the entire disclosure of which is expressly incorporated herein by reference. Additionally, this application is a continuation-in-part of and copendinq U.S. patent application Ser. No. 11/193,020 entitled "Methods and Apparatus for Treating Disorders of the Ear, Nose and Throat" filed on Jul. 29, 2005.

FIELD OF THE INVENTION

The present invention relates generally to medical devices and methods and more particularly to minimally invasive, devices, systems and methods for treating sinusitis and other ear, nose & throat disorders.

BACKGROUND

Balloon angioplasty catheters have been used to treat cardiovascular disorders for many years. In general, balloon angioplasty catheters of the prior art have included over-the-wire catheters, which ride over a separate guide wire, which represent the majority of balloon catheters, fixed-wire catheters, which combine the balloon catheter and guide wire into one device, and rapid exchange catheters, which are essentially over-the-wire type catheters with short guidewire lumens that allow the catheter to be exchanged without the use of an extension wire.

The fixed wire balloon angioplasty catheters of the prior art have typically ranged in length from about 120 cm to about 150 cm and have had balloon dimensions and flexural properties that were suitable for performing balloon angioplasty procedures in coronary or peripheral blood vessels. Examples of commercially available fixed-wire balloon angioplasty catheters include the Ace™ balloon catheters (Boston Scientific, Inc., Natick, Mass.).

More recently, procedures have been developed wherein balloon catheters are used to dilate the ostia (or other openings) of paranasal sinuses for the treatment of disorders such as sinusitis. In these procedures, a balloon catheter or other dilator catheter is advanced transnasally into an opening of a paranasal sinus and used to dilate that opening, thereby improving drainage and ventilation of the affected sinus. In some embodiments, a guide catheter is initially inserted into the nose, a guidewire is then advanced through the guide catheter and the balloon catheter is then advanced over the guidewire. In other embodiments, as described in parent application U.S. patent application Ser. No. 11/150,847, issued as U.S. Pat. No. 7,803,150, the balloon catheter may be equipped with a non-removable guide member that extends from its distal end and is advanceable through the ostium of the paranasal sinus ahead of the catheter shaft and balloon. The provision of such non-removable guide member extending from the distal end of the balloon catheter eliminates the need for use of a separate guidewire, thereby simplifying the procedure, shortening the procedure time, reducing the need for an assistant, and decreasing the amount of radiation exposure to the patient and operator due to use of fluoroscopy.

There remains a need in the art for further development and refinement of balloon catheters (and other dilator devices) that have non-removable guide members for use in dilating the ostia of paranasal sinuses.

SUMMARY OF THE INVENTION

In accordance with the present invention, there is provided a balloon catheter device for dilating an opening of a paranasal sinus in a human or animal subject. In general, this balloon catheter device comprises; (a) a catheter shaft having a proximal end and a distal end, (b) a non-compliant or semi-compliant balloon (or other suitable dilator) mounted on the catheter shaft, such balloon being positionable within the opening of the paranasal sinus while in a non-inflated state and thereafter inflatable to an inflated state such that it will cause dilation of the opening of the paranasal sinus, (c) at least one position indicating element useable to determine when the balloon is positioned within the opening of the paranasal sinus and (d) a non-removable guide member, at least a portion of which extends from the distal end of the catheter shaft, said non-removable guide member having a limited range of axial movement or no movement relative to the catheter shaft, said non-removable guide member being advanceable through the opening of the paranasal sinus ahead of the catheter shaft. Such balloon catheter device has a length less than about 20 cm. In some embodiments, the guide member may be attached to the catheter device in a substantially fixed position. In other embodiments, the guide member may be attached to the catheter device in a manner that allows the guide member to undergo rotational movement and/or some limited range of longitudinal movement (e.g., axial translation). In some embodiments the guide member may extend through all or part of the catheter shaft, with only a portion of the guide member protruding beyond the distal end of the catheter shaft. In other embodiments, the guide member may be attached to the distal end of the catheter shaft such that little or no part of the guide member actually extends into the catheter body. In some embodiments, the catheter shaft may be formed of plastic while in other embodiments the catheter shaft may be formed of metal (e.g., hypotube). In some embodiments, the catheter device may be used in conjunction with a straight or curved guide catheter. In other embodiments, the catheter device may be inserted into the opening of a paranasal sinus without the use of a guide catheter.

Further in accordance with the invention there is provided a guide catheter through which the above-summarized balloon catheter device may be inserted. Such guide catheter may comprise an outer metal tube and a plastic tube that extends coaxially through the lumen of the metal tube with a distal portion of the plastic tube extending out of and beyond the distal end of the metal tube. The portion of the plastic tube that extends beyond the distal end of the metal tube may be straight or curved. In some embodiments, an outer cover may extend over all or part of the outer surface of the guide catheter and such outer cover may serve to smooth the transition between the distal end of the metal tube and the adjacent surface of the protruding portion of the plastic tube. In some embodiments, an inner liner (e.g., a lubricious liner) may line all or part of the lumen of the inner plastic tube.

Still further in accordance with the present invention, there is provided a method for dilating an opening of a paransal sinus in a human or animal subject. This method generally comprises the steps of; (A) providing a balloon catheter that has a non-removable guide member that extends from its distal end, (B) trans-nasally inserting the balloon catheter and causing at least part of the non-removable guide member to pass through an opening of the paranasal sinus, (C) moving the balloon catheter to a location where the balloon is positioned within the opening of the paranasal sinus and (D) inflating the balloon to cause dilation of the opening of the paranasal sinus.

Further aspects, details and embodiments of the present invention will be understood by those of skill in the art upon reading the following detailed description of the invention and the accompanying drawings.

BRIEF DESCRIPTION OF THE DRAWINGS

FIG. 2A is a cross sectional view through line 2A-2A of FIG. 2.

FIG. 2B is a cross sectional view through line 2B-2B of FIG. 2.

FIG. 2C is a cross sectional view through line 2C-2C of FIG. 2.

FIG. 2D is a cross sectional view through line 2D-2D of FIG. 2.

FIG. 2F is cross sectional view through the longitudinal axis of yet another alternative embodiment of a non-removable wire balloon catheter of the present invention.

FIG. 3 is a partially sectioned side view of the non-removable guidewire component included in the balloon catheters shown of FIGS. 1A, 2E and 2F.

FIG. 4 is a partial longitudinal sectional view through a balloon catheter of the present invention showing an alternative construction at the location where the proximal end of the balloon is mounted on the outer catheter shaft.

FIG. 8A is an enlarged view of a distal portion of FIG. 8.

DETAILED DESCRIPTION

The following detailed description and the accompanying drawings are intended to describe some, but not necessarily all, examples or embodiments of the invention. The contents of this detailed description and the accompanying drawings do not limit the scope of the invention in any way.

The term "opening of a paranasal sinus" as used herein shall, unless otherwise stated, include any and all trans-nasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc. Other non-limiting examples of diagnostic or therapeutic substances that may be useable in this invention are described in copending U.S. patent application Ser. No. 10/912,578 entitled Implantable Devices and Methods for Delivering Drugs and Other Substances to Treat Sinusitis and Other Disorders filed on Aug. 4, 2004, issued as U.S. Pat. No. 7,361,168 on Apr. 22, 2008, the entire disclosure of which is expressly incorporated herein by reference.

The term "nasal cavity" as used herein shall, unless otherwise stated, be broadly construed to include any cavity that is present in the anatomical structures of the nasal region including the nostrils and paranasal sinuses.

The term "trans-nasal" as used herein shall mean through a nostril.

Figure 5A:
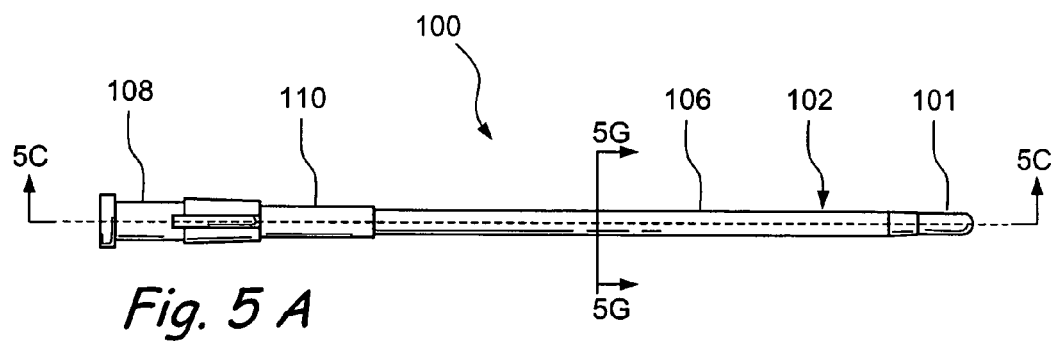
FIG. 5A is another side view of the guide catheter of FIG. 1B, with the catheter rotated 90 degrees from that seen in FIG. 1B.
Figure 5B:
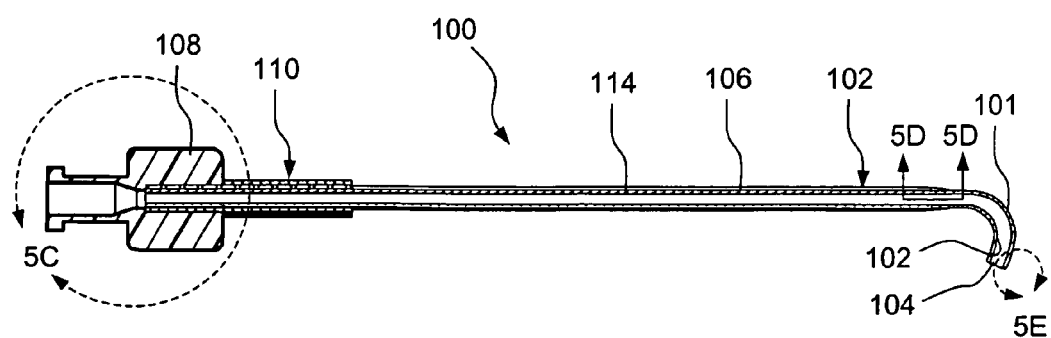
FIG. 5B is a cross sectional view through line 5C-5C of FIG. 5A.
Figure 5C:
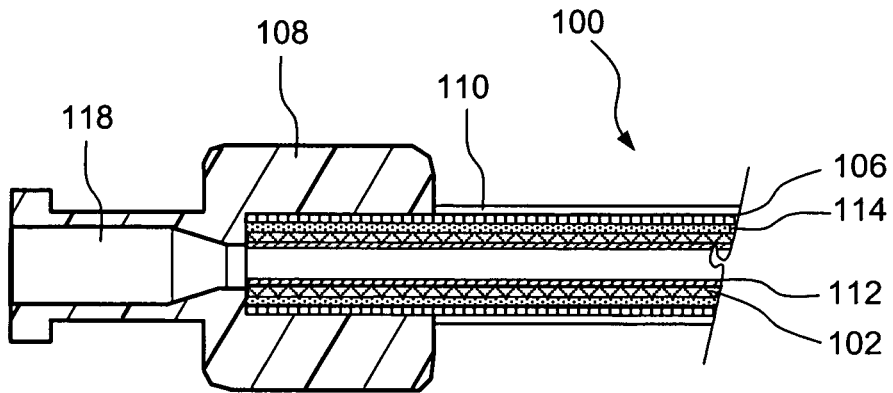
FIG. 5C is an enlarged view of region 5C of FIG. 5B.
Figure 5D:
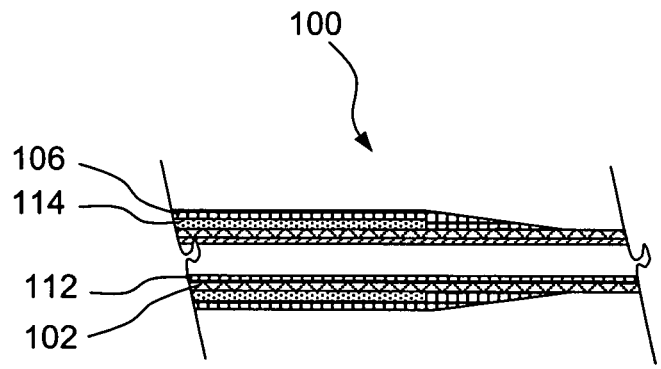
FIG. 5D is an enlarged cross sectional view through Line 5D-5D of FIG. 5B.
Figure 5E:
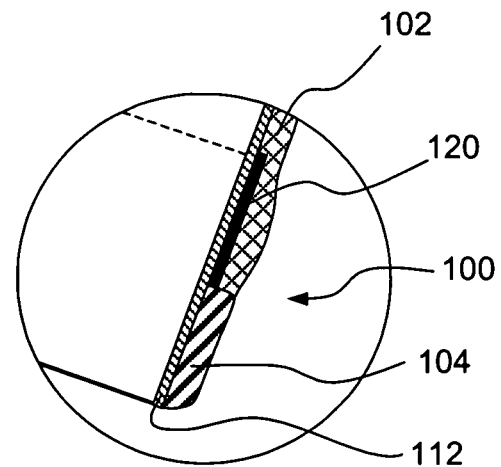
FIG. 5E is an enlarged view of region 5E of FIG. 5B.
Figure 5F:
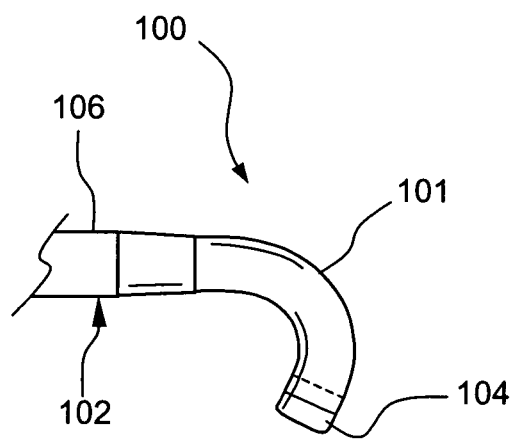
FIG. 5F is an enlarged view of region 5F of FIG. 1B.
Figure 5G:
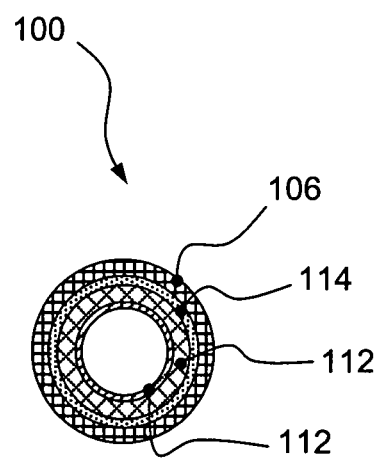
FIG. 5G is a cross sectional view through line 5G of FIG. 5A.
Figure 6:
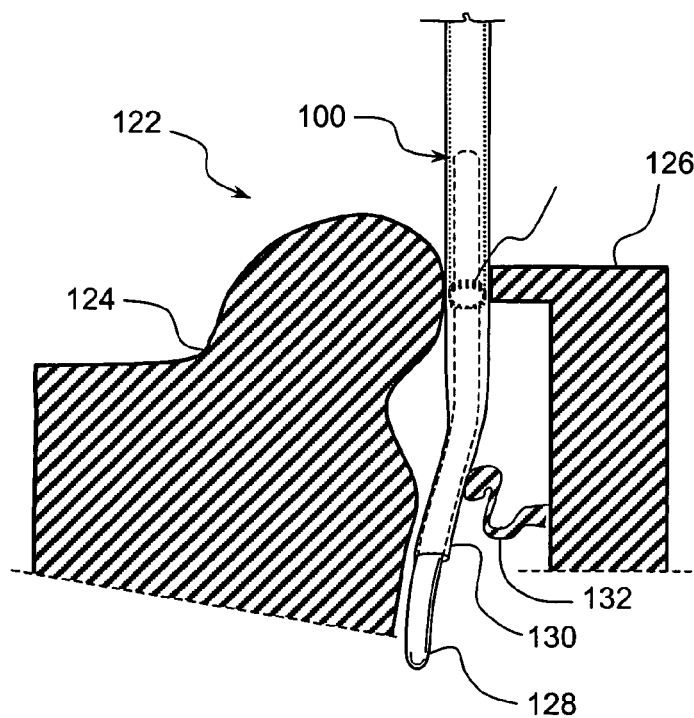
FIGS. 6A and 6B are schematic diagrams showing a device and method for forming the curve in the guide catheter of FIG. 1B.
Figure 6:
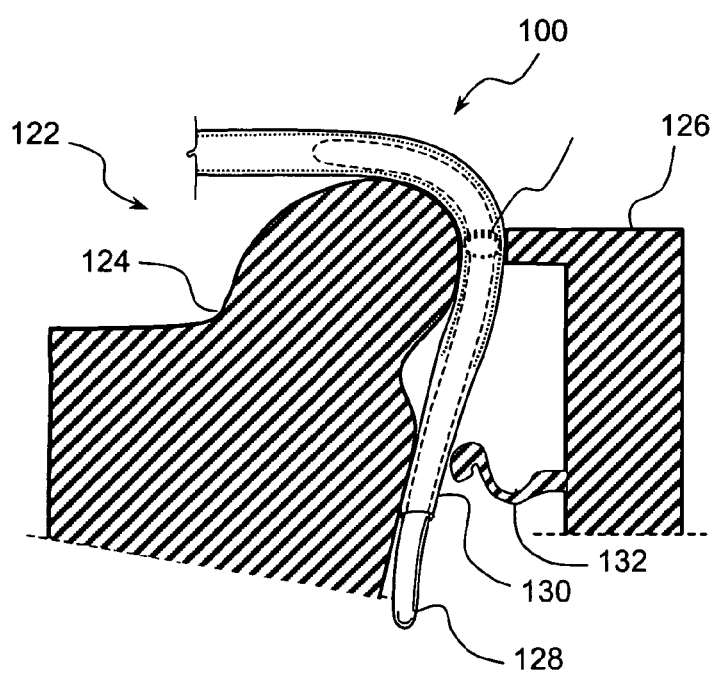

In general, FIGS. 1-5H show catheters devices of the present invention, FIGS. 6A and 6B show a device and method for forming a curve in a guide catheter device of the present invention and FIGS. 7A-7E show one embodiment of a method for using catheter devices of the present invention to treat sinusitis in a human subject.

Figure 1:
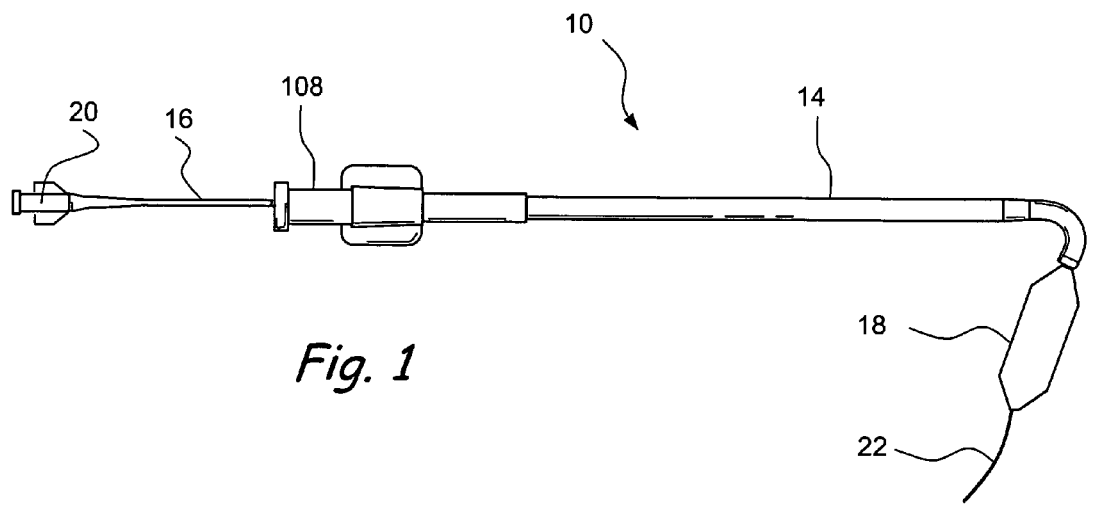
FIG. 1 shows a side view of a guide catheter/non-removable wire balloon catheter system of the present invention.
Figure 2:
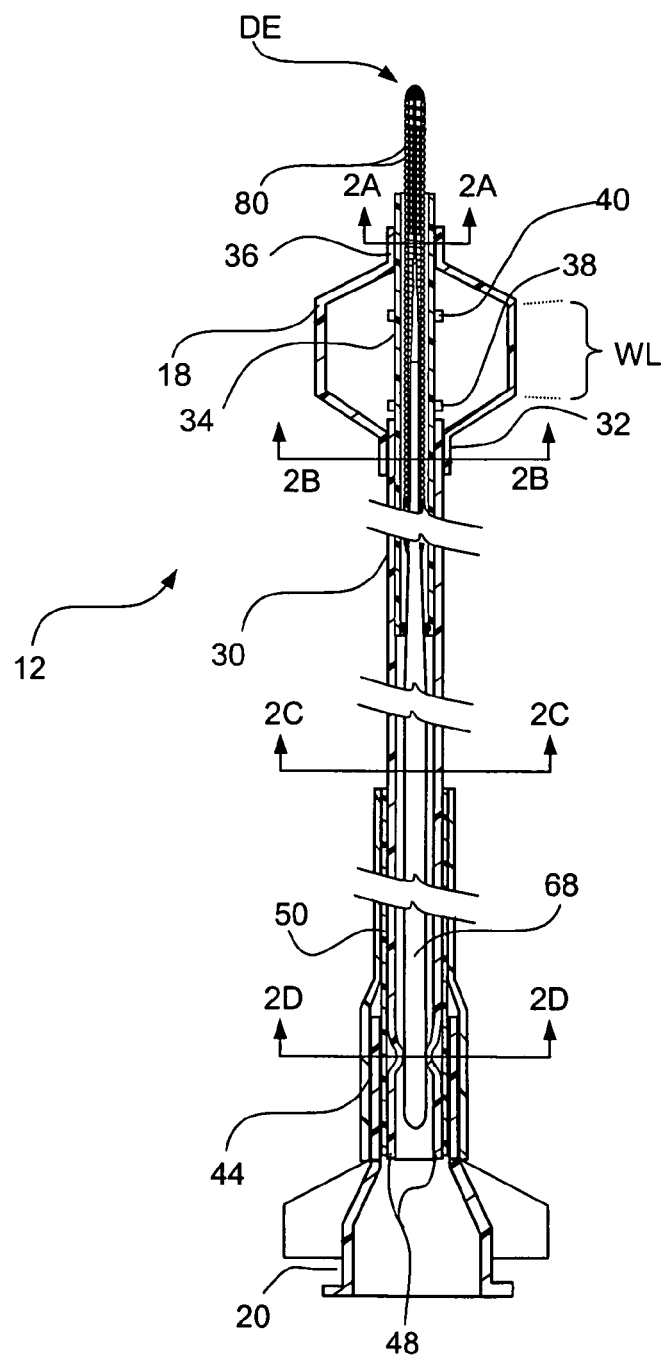
FIG. 2 is a cross sectional view through the longitudinal axis of the non-removable wire balloon catheter of FIG. 1A.

With reference to FIGS. 1-2D, one embodiment of a system 10 of the present invention comprises a non-removable wire balloon catheter 12 and a guide catheter 14. Although shown and described as a system it is to be appreciated that the non-removable wire balloon catheter 12 and guide catheter 14 need not necessarily be used in combination, but rather may also be used independently of one another.

Non-Removable Wire Balloon Catheter

Figure 2E:
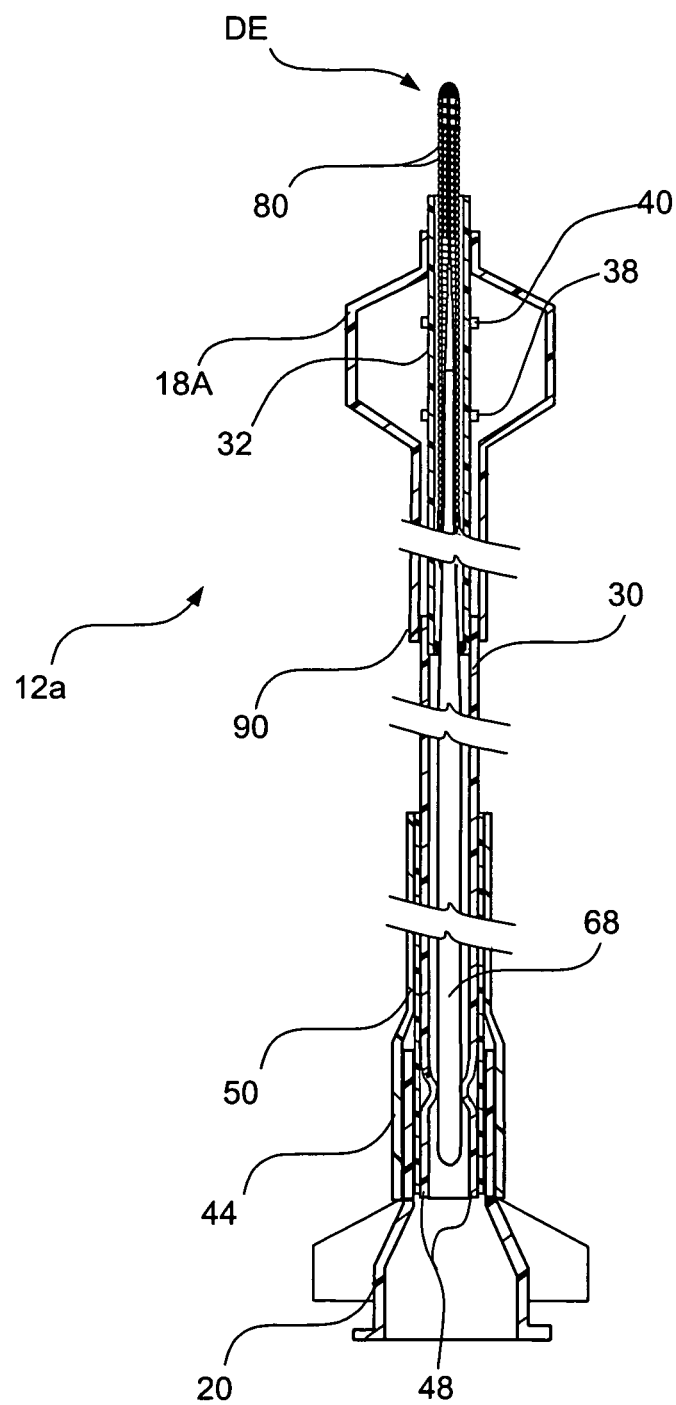
FIG. 2E is cross sectional view through the longitudinal axis of an alternative embodiment of a non-removable wire balloon catheter of the present invention.
Figure 2:
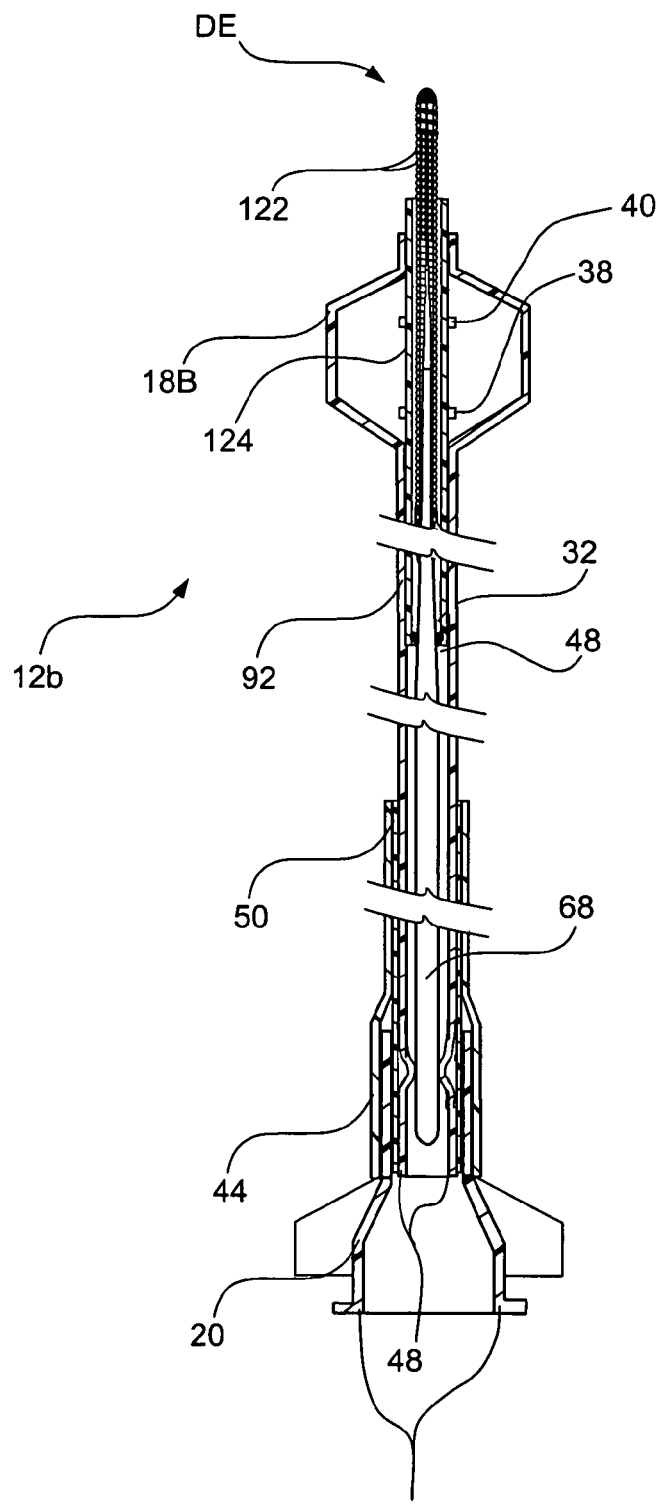

The embodiment of the non-removable wire balloon catheter 12 shown in FIGS. 1-2E comprises an elongate, flexible catheter shaft 16 having a balloon 18 mounted thereon. A proximal Luer hub 20 is attached to the proximal end of the catheter shaft 16. An inflation device (not shown) may be attached to the Luer hub 20 and used to inflate and deflate the balloon 18. A non-removable guide member 22 extends out of and beyond the distal end DE of the catheter shaft 16.

In one preferred embodiment for adult applications, balloon catheter 12 has an overall length of approximately 43.5 cm and its shaft 16 has an outer diameter of about 0.058 inches.

As seen in FIG. 2, in this embodiment, the catheter shaft 16 comprises an outer tube 30 which extends from the hub 20 through the proximal end 32 of balloon 18. An inner tube 34 is positioned coaxially within the outer tube 30 and extends from the mid-region of the outer tube 30 and through the distal end of the balloon 36. As shown, the proximal end of the balloon 32 is attached by adhesive, thermal bonding or other suitable means to the outer surface of the outer tube 30 and the distal end of the balloon 36 is attached by adhesive, thermal bonding or other suitable means to the outer surface of the inner tube 34. The balloon has a cylindrical sidewall with tapered portions adjacent to the proximal end 32 and distal end 36. The length of the cylindrical portion of the balloon 18 is referred to herein as the balloon's working length WL. The working length WL of balloon 18 may, in some embodiments, range from 4 mm to 35 mm. In one preferred embodiment, the working length of the balloon is around 16 mm+/−1 mm. In another preferred embodiment, the working length of the balloon is around 24 mm+/−1 mm. Balloon 18 may be inflated to a suitable working pressure of around 12 to 16 atmospheres.

Optionally, position indicators, such as radiopaque markers 38, 40 may be mounted on the inner tube 34 within the balloon 18 to mark the locations of the proximal and distal ends of the working length WL. Balloon 18 may be coated with one or more balloon coatings including, but not limited to puncture resistance coating, abrasion resistance coating, anti-tack coating, lubricous, hydrophilic, etc. In a particular embodiment, balloon 18 is made of PET of a wall thickness around 0.001 inches coated by a 0.001 inch thick polyurethane coating with a tensile strength of 12,000 to 16,000 psi and a burst pressure of more than 16 atmospheres. In some embodiments, a portion of the non-removable guide member 22 may extend through the balloon 18 and that portion of the non-removable guide member 22 may be radiopaque or otherwise radiographically distinguishable from the rest of the non-removable guide member 22 so as to indicate the position of balloon 18 as well as the position of the non-removable guide member distal end.

As seen in FIGS. 2 and 3, the non-removable guide member 22 of this embodiment extends fully through the catheter shaft 16 such that only a portion of this guide member 22 protrudes beyond the distal end of the catheter shaft 16. The guide member 22 is constructed to impart differing degrees of stiffness to different regions of the catheter shaft 16. In this regard, as may be best appreciated from FIG. 3, the guide member 22 generally comprises a proximal portion or region 60, a middle portion or region 62 and a distal portion or region 64. This guide member 22 is constructed of a core wire 66, an outer coil 68 and an inner coil 70. In some embodiments, the core wire may be of constant diameter over its entire length. However, in the example shown, the core wire 66 has sections of differing diameter and, hence, differing stiffness. In this example, a proximal section 68 of core wire 66 makes up the proximal region 60 of guide member 22 and is of uniform constant diameter, typically in the range of 0.014 mm to 0.038 in some embodiments and of 0.025+/−0.0005 inch in other embodiments. The particular diameter and/or rigidity of this proximal portion or region 60 may be selected to provide sufficient support to the balloon while remaining small enough to reduce shaft profile and inflation and deflation time of the balloon.

Within the middle region 62 of the guide member 22, the core wire 66 has a number of stepped down areas, namely a first tapered section 72, a first constant diameter section 74 of uniform constant diameter (e.g., in the range of 0.006 to 0.012 inches), a second tapered section 76 and a second constant diameter section 78 of uniform constant diameter (e.g., in the range of 0.002 to 0.008 inches). The distal region 78 of constant diameter may have some or all of its length flattened or partially flattened to fine tune the distal flexibility of the guidewire. The guidewire should be very flexible near the proximal end of region 64 to enable the guidewire to conform to the internal contours of the sinus anatomy. In some embodiments, this distal section 80 of the core wire 66 may be flattened (e.g., cut, swaged, etc.) while the remaining portions of the core wire 66 may be substantially round. In embodiments where the distal section 70 of the core wire 66 is flattened, the height of the flat is generally between from about 0.001 inch to about 0.004 inch. Such flattening of the distal section 70 of the core wire 66 accomplishes the purpose of making the distal region 64 more flexible in one plane (e.g., up and down) than in another plane (e.g., side to side), thereby rendering the distal portion 64 more likely to form a smooth curl within the sinus cavity as it is advanced through the sinus opening.

An outer helical coil, such as a stainless steel wire coil, is affixed to the first tapered section 72 within the middle region 62 and extends to the distal tip of the guide member 22. An inner helical coil, platinum/tungsten alloy, is disposed within the outer coil 70 and around part of the distal section 80 of the core wire 66, as shown. This construction forms an atraumatic tip that is sufficiently stiff to pass through the nasal and paranasal anatomy and floppy enough to buckle without causing damage to the nasal and paranasal tissue. The platinum/tungsten alloy provides a radiopaque marker to identify the tip of the non removable guide member 22 when viewed fluoroscopically.

Two design parameters, namely the diameters and/or relative stiffness of the various sections 68, 72, 74, 76, 78, 80 and material of which the core wire 66 is constructed, can be of particular importance in allowing the non-removable guide member 22 to achieve its desired function. In the preferred embodiment, core wire 66 is made of nickel-titanium alloy (Nitinol) which has high elasticity. The high elasticity of the nickel-titanium core wire 66 enables the balloon catheter shaft 16 to pass easily through regions of guide catheter 14 that have sharp bends or curves without kinking of the core wire 66. The constant diameter section 74 is the region where the balloon is located. The diameter of this section should be small enough to avoid creating excessive stiffness which would create resistance when advancing the balloon catheter through the tip of the guide catheter. However, the diameter of region 74 must be large enough to prevent guidewire buckling and support the balloon as the catheter is advanced. Most importantly, the diameter of region 74 and the gradual taper of region 76 must allow the guidewire to bend in a relatively smooth arc without kinking where the non removable guide member 22 exits the distal end of the balloon 18. In one embodiment the optimal diameter of constant diameter section 74 has been determined to be between 0.006 to 0.012 inches. This diameter can be used to develop catheters for various sinus anatomies and locations. For instance, a catheter designed to extend a significant distance out the tip of a relatively straight guide could use a larger diameter. A catheter for use in a shaped guide needs a smaller diameter to reduce resistance through the guide. The length of non-removable guide member 22 extending out the distal end of the balloon 18 should be long enough to partially define the outline of the sinus cavity when viewed fluoroscopically but not so long that an excessive length of guidewire tip must be advanced into small sinus cavities. In a preferred embodiment, the length is between about 3 cm and about 6 cm.

The proximal end of the outer tube 30 is received within hub 20 and an outer sleeve 44 may be formed about the area where the outer tube 30 enters the hub 20. Labeling may be printed on this sleeve 44 and, optionally, this sleeve 44 may act as a strain relief member.

As seen in FIGS. 2 and 2D, a crimpable member such as a metal hypotube 48 is attached to the proximal end of section 68 of core wire 66 and extends into the hub 20, where it is surrounded by a plastic hypotube cover 50. The hypotube 48 is crimped inwardly so as to frictionally engage and hold the proximal section 68 of core wire 66 within hub 20. As seen in the cross section view of FIG. 2D, the hypotube 48 may be crimped at discrete locations so as to provide flow channels 90 through which balloon inflation fluid may flow.

Figure 1A:
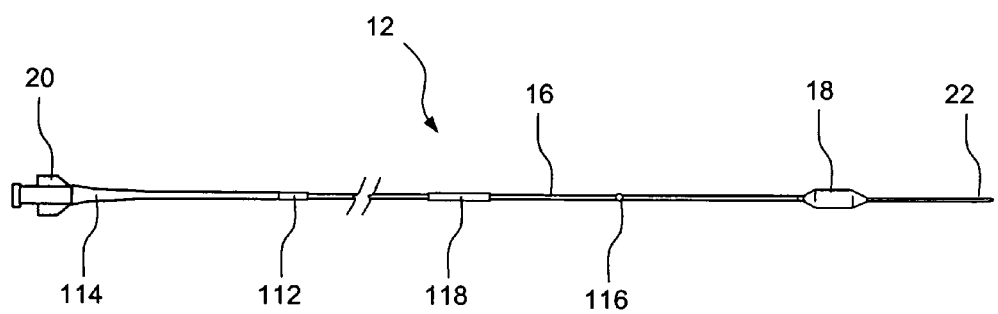
FIG. 1A is a side view of the non-removable wire balloon catheter shown in FIG. 1.
Figure 1B:
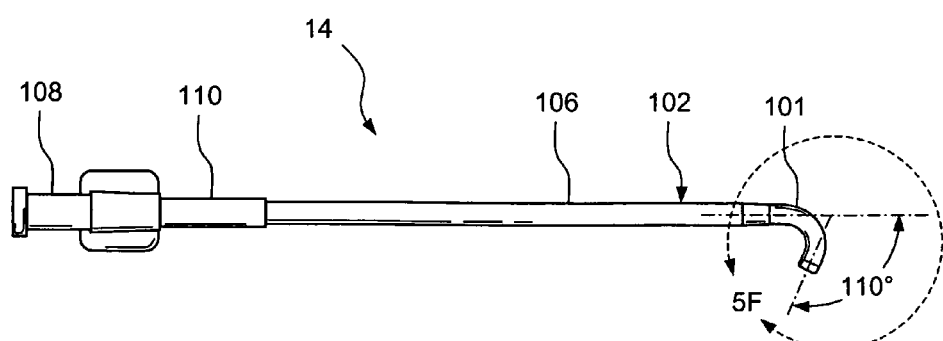
FIG. 1B is a side view of the guide catheter shown in FIG. 1.

As shown in FIG. 1A, a short distal marker 116 and a long proximal marker 118 may be formed on the catheter shaft 16. Distal marker 116 and long proximal marker 118 enable the user to determine the relative location of various regions of balloon catheter device 12 relative to the distal tip of guide catheter 14 without requiring the use of fluoroscopy. For example, the distal marker 116 may be approximately 1.5 mm long and long proximal marker 118 may be approximately 20 mm long. Also, the distal end of distal marker 116 may be located approximately 127 mm from the distal tip of guide member 22 and the proximal end of long proximal marker 93 may be located approximately 131 mm from the proximal end of the balloon 18. These markers 116, 118 are useable in various ways. For example, as described more fully herebelow, the balloon catheter 12 may be useable in conjunction with a specially sized guide catheter 14 as seen in FIG. 1B. In typical usage, the distal end of the non-removable guide member 22 will be inserted into the proximal Luer hub 108 of guide catheter 14 and the balloon catheter 12 will be advanced through the guide catheter 14. The balloon catheter 12 may be sized relative to the guide catheter 14 such that, when the distal marker 116 is even with and about to enter the proximal end of the Luer hub 108 of guide 14, the distal end DE of non-removable guide member 22 will be even with and about to emerge out of the distal end DE of guide catheter 14. Also, when the proximal end of long proximal marker 118 is even with the Luer hub 108 of guide 14, the end of the balloon 36 will be even with and about to emerge out of the guide catheter 14. Also, when the proximal end of long proximal marker 118 is even with and about to enter the proximal end of the Luer hub 108 of guide 14, the proximal end of the balloon 32 will be even with the distal end of the guide catheter 14 and the entire balloon 18 will have emerged out of the distal end of the guide catheter 14.

In embodiments where the balloon catheter 12 is to be inserted through a curved guide catheter 14, it may be desirable to design the proximal joinder of the balloon 18 to the catheter shaft 16 in such a way as to minimize the likelihood for snagging or catching of the proximal end 32 of the balloon 18 as the balloon catheter 14 is pulled back through the curved portion of the guide. FIGS. 2E and 2F show alternative embodiments of the balloon catheter 10a, 10b which are designed to accomplish this. Also, FIG. 4 shows an alternative construction of the catheter shaft 16 at the location where the proximal balloon end 32 is affixed to the catheter shaft 16.

The balloon catheter 10a shown in FIG. 2E is the same as that shown in FIG. 2, except that in the catheter 10a of FIG. 2E the balloon 18A is formed in the distal portion of an elongated balloon tube member 90 which extends proximally to a location near the middle of the catheter shaft where it is bonded to outer tube 30. In this manner, the seam between the proximal end of balloon tube member 90 and outer tube 30 is located proximally enough to avoid any passing through (or being retracted through) the curved region of the guide catheter 14.

The balloon catheter 10b shown in FIG. 2F is the same as that shown in FIG. 2 except that in the catheter 10b of FIG. 2F, the outer tube 30 is absent and an elongated balloon tube 92 extends all the way to the proximal end of the catheter body where it is received within the sleeve 44 and is bonded to hypotube 48. In this manner, the catheter body is essentially seamless from the balloon 18n all the way proximal to the hub 20, thereby eliminating any potential for a seam to snag or catch on the curvature in the guide catheter 14.

With reference to FIG. 4, in some embodiments of the catheter device 10 such as that shown in FIGS. 1-2D, a modified outer tube 30a may be used wherein the outer diameter of such outer tube 30a is reduced at the location where the proximal end 32 of the balloon 18 is affixed, thereby providing a smoothed transition and deterring the proximal end 32 of balloon 18 from snagging or catching as it is retracted through a curved guide catheter or the like.

Guide Catheter

An example of the preferred guide catheter 14 is shown in FIGS. 2B and 5A-5G. As shown, the guide catheter 14 comprises an elongate shaft 102. Guide catheter 14 is made of suitable biocompatible materials as described below. The distal portion of the shaft 102 incorporates a curve 101. Various embodiments of guide catheter 14 may be designed with unique curves formed therein to access specific anatomical locations. Or, in some embodiments, the guide catheter shaft 102 may be malleable so that the operator may form the shaft 102 to a desired shape prior to or during the procedure. In another embodiment (not shown), the guide catheter 14 shaft may be straight, without any curvature. Guide catheters 14 having different angles A of curve 101 may be used, for example, to access one or more anatomical regions in the nasal cavity including, but not limited to ostia of various paranasal sinuses.

In the example shown in the drawings, the elongate shaft 102 of the guide catheter 14 is formed of an outer metal tube such as a hypotube 114 having a plastic tube 112 extending coaxially therethrough with a distal portion 100 of the plastic tube 112 protruding out of and beyond the distal end of the hypotube 114, as seen in FIG. 5F. The hypotube in this example is traditional stainless steel hypotube material. However, it will be appreciated that this hypotube 114 element may be formed of any suitable material having the desired stiffness, such as stainless steel, titanium, nickel-titanium alloys (e.g., Nitinol), polymers such as Nylon, etc. The plastic tube 112 formed of suitable material such as Nylon or other thermoplastic. In the embodiment shown, the radius of curvature of the curve 101 is 0.18 inches. In the embodiment shown, the outer diameter of the flared distal end of elongate shaft 102 is 0.113+/−0.003 inches and the length of radiopaque marker is 0.04 inches. The length of atraumatic tip 104 ranges from 0.060 to 0.120 inches. The outer rim of atraumatic tip 104 is radiused. The distal end of outer sleeve 106 is tapered as shown and covers elongate shaft 102. In a preferred embodiment shown, the outer diameter of the distal end of outer sleeve 106 is 0.109+/−0.003 inches.

Optionally, an outer sleeve or cover 106 may be disposed over a portion of the outer surface of hypotube 114 and, in some cases, may extend over at least some of the protruding distal portion 100 of the plastic tube 112, thereby providing a smooth outer surface over the area where the distal end of the hypotube 114 is located. Such outer sleeve or cover 106 may be formed of any suitable material such as Nylon or other heat shrinkable thermoplastic.

Also optionally, an inner liner 111 may extend through and line the wall of the lumen of plastic tube 112. This inner liner 111 may be formed of any suitable material, and preferably a lubricious material, such as polytetrafluoroethylene PTFE or the like.

In a preferred embodiment, guide device 14 is of a smaller outer diameter than has been previously known for transnasal treatment of paranasal sinuses. The construction of the embodiment allows for greater access and less trauma to a larger number of patient's sinuses, particularly the maxillary sinuses. The smaller diameter allows for the use of the guide catheter alongside other instruments, like an endoscope, in the constricted paranasal anatomy. A shorter or more compact tip allows for greater maneuverability in the tortuous and constricted anatomy. The smaller diameter of the guide allows easier, less traumatic passage in the paranasal cavities. For example, it is easier to fit between the nasal septum and the middle turbinate when accessing the sphenoid; easier fit into the middle meatus and between the lateral wall of the middle turbinate and the uncinate process and lamina papyricia when accessing the maxillary, frontal, and ethmoid sinuses; easier to fit in the middle meatus and up into the frontal recess when accessing the frontal sinus. Additionally, the tight/small diameter of the distal curve of the guide allows less damage/trauma to the middle turbinate and uncinate when accessing the maxillary sinus. When the guide is torqued such that the curve of the guide (the plane of the curve) is essentially perpendicular to the middle turbinate and uncinate process, it will be easier to fit a smaller curve in that narrow space between the middle turbinate and the uncinate/infindiubulum. Additionally, when accessing the maxillary sinus, the smaller diameter guide tip (not curvature radius, but actual diameter of the tip) is better able to slip behind the uncinate (or between the uncinate and lateral wall) and then access the maxillary sinus. With a larger guide catheter, it is not uncommon for the surgeon to tease forward the uncinate process because he was not able to slip the bigger guide catheter tip behind the uncinate process. It is especially useful in accessing the maxillary sinus where the guide catheter tip must be advanced in one orientation to pass by the middle turbinate and then rotated to "hook" the distal end around the uncinate process to give access to the maxillary ostium. In the preferred embodiment, the outer cover 106 is made of a length of Nylon 11 tubing with an inner diameter of 0.125+/−0.001 inches and an outer diameter of 0.139+/−0.001 inches. Outer cover 106 substantially surrounds the outer surface of the hypotube and a region of elongate shaft 102 emerging from the distal end of the hypotube after it is fused/laminated to these underlying surfaces. The final diameter of the shaft over the hypo tube region is 0.134+/−0.003". This embodiment comprising outer cover 106 is especially useful for providing an outer lubricious surface on guide device 14, for improving joint integrity between the hypotube and elongate shaft 102, and creating a smooth transition between the distal portion of elongate shaft 102 and the distal end of the hypotube. The proximal end of guide device 14 comprises a hub 108. In the embodiment shown, hub 108 is a female Luer hub. The portion of outer cover 106 extending beyond the distal end of hub 108 is covered with a length of label tubing 110 as shown. The length of label tubing 110 may range from 0.5 inches to 1 inch. In an embodiment where the guide catheter 14 has a curve 101 of 110 degrees and is intended for use in accessing a maxillary sinus, the label tubing 110 may be labeled with the code "M-110", wherein the "M" stands for maxillary sinus and the "110" stands for the angle of the curved region 101. The length of the portion of the guide device 14 that enters the body may range preferably from 3 inches to 5 inches, and the length of the portion that remains outside of the body is preferably at least 0.5 inches. The overall length of guide device 14 measured from the distal end of hub 108 to the distal tip of guide device 14 measured along a curved distal region of elongate shaft 102 is 4.25+/−0.25 inches. The length of guide device measured from the proximal end of hub 108 to the distal tip of guide device 14 measured along a curved distal region of elongate shaft 102 is 5.16+/−0.15 inches. The inner surface of guide device 14 may be lined by a lubricious coating or a tubular lubricious liner (not shown). Such a lubricious coating or tubular lubricious liner is useful to facilitate passage of one or more devices through the lumen of guide device 14 especially when guide device 14 comprises an angled, curved or bent region. Proximal portion of guide device 14 may comprise a rotating valve device (not shown) such as a Touhy-Borst device to lock down a device such as a sheath, guidewire, balloon catheter or other devices that are being inserted through guide device 14. The distal region of guide device 14 disclosed has a radiopaque marker 120 (see FIGS. 5E and 5F). The radiopaque marker may be made of suitable biocompatible materials including, but not limited to, metals, polymers loaded with a radiopaque substance, etc. In one embodiment, multiple guide devices 14 of varying designs are provided in a kit.

FIG. 5B shows a longitudinal sectional view of the guide device 14. The outer diameter of elongate shaft 102 is around 0.113+/−0.001 inches and the inner diameter of elongate shaft 102 is around 0.095+/−0.001 inches prior to being fused/laminated to the underlying tubing. In a preferred embodiment, the material of elongate shaft 102 has Rockwell hardness in the range of about 70R to about 110R. In this preferred embodiment, the distal portion of elongate shaft 102 is flexible enough to prevent or reduce damage to the anatomy. Yet, the distal portion is rigid enough to retain its shape as one or more devices are passed through guide device 14. Furthermore, the distal portion of elongate shaft 102 is rigid enough to enable a user to use the distal portion to displace paranasal structures. The distal portion of elongate shaft 102 comprises a curved or angled region 101 curved at an angle ranging from 0 degrees to 135 degrees. In a preferred embodiment, the inner surface of elongate shaft 102 is lined by a lubricious coating or a tubular lubricious liner 112 made of a suitable biocompatible material such as PTFE. In one embodiment, the inner diameter of lubricious liner 112 in guide device 14 is 0.087+/−0.003 inches. In one embodiment, lubricious liner 111 is made from a PTFE tube of outer diameter 0.093+0.0/−0.001 inches and an inner diameter of 0.089+/−0.001 inches which shrinks to about 0.087+/−0.003 inches upon bonding to inner surface of the elongate shaft 102. A radiopaque marker 120 (shown in FIG. 1F) is located in the distal region of elongate shaft 102 between plastic tube 112 and lubricious liner 112. The liner 111 extends beyond the distal end of plastic tube 112 and underlying marker 120 and the atraumatic tip member 104 is disposed about and secured to the distal end of the liner 111, as seen in the enlarged view of FIG. 5E. The atraumatic tip 104 may be formed of suitable biocompatible materials including, but not limited to a polyether block amide (Pebax 40D). Atraumatic tip 104 prevents or reduces accidental damage to the anatomy caused by the distal tip of guide device 14. In one embodiment, length of atraumatic tip 104 ranges from 0.060 to 0.120 inches. The material of atraumatic tip 104 can have a Shore Durometer hardness in the range of about 35D to about 72D. Guide device 14 further comprises a hypotube 114 to which elongate shaft 102 and outer cover 106 are attached. In a preferred embodiment, the outer diameter of hypotube 114 is 0.120+/−0.001 inches and the inner diameter is 0.112+/−0.002 inches. In a preferred embodiment of guide device 14, no portion of hypotube 114 is exposed to bodily fluids. In one embodiment of a method of constructing guide device 14, a stainless steel hypotube 114 is bonded to an elongate shaft 102 such as a Nylon tube to increase the strength of elongate shaft 102. In one embodiment of bonding hypotube 114 to elongate shaft 102, hypotube 114 is heat bonded to elongate shaft 102. One or more openings, perforations or holes may be located on hypotube 114 to enable material of elongate shaft 102 to melt into the one or more openings, perforations or holes. When the melted material of elongate shaft 102 solidifies, an additional mechanical bonding is created between hypotube 114 and elongate shaft 102. In another embodiment of bonding hypotube 114 to elongate shaft 102, hypotube 114 is bonded to elongate shaft 102 by an adhesive. The proximal end of guide device 14 comprises hub 108. In the embodiment shown, hub 108 is a female luer hub. In a preferred embodiment, the luer taper on such a female luer hub conforms to ISO 59471-1986 and ISO 59472-1991. Hub 108 may be attached to the outer surface of outer sleeve 106. In one embodiment, hub 108 is attached to the outer surface of outer sleeve 106 by a suitable biocompatible adhesive e.g. Dymax 1191. Hub 108 has two wings to enable a user to turn guide device 14. In a preferred embodiment, the two wings are located in the same plane as the plane of a curve on the distal region of elongate shaft 102 to assist the user in knowing where the tip of guide device 14 is pointing. In another embodiment, one wing can be longer than the other or have another indicia of which side of the device the curved tip of located. The guide device design shown in FIGS. 1A-1C is especially suited for trans-nasal access of the maxillary sinuses.

In a preferred embodiment, the length of atraumatic tip 104 ranges from 0.060 to 0.120 inches. The outer and/or inner rim of the distal end of atraumatic tip 104 may be radiused to reduce or eliminate sharp edges which in turn reduces or minimizes injury to tissue during the use of guide device 14. In one embodiment, the radius of curvature of the radiused outer and/or inner rim ranges from 0.005 to 0.012 inches. In a preferred embodiment, the tubular element is made of Pebax 40D and has an outer diameter ranging from 0.115+/−0.001 inches and an inner diameter ranging from 0.095+/−0.001 inches. Atraumatic tip 104 is fused to shaft 102 to form a butt joint. The tubular element is preferably designed using a suitable material of construction and a suitable manufacturing process such that there is negligible color bleeding from atraumatic tip 104. The distal end of guide device 14 also comprises a radiopaque marker 120. In the embodiment shown, radiopaque marker 120 is located between the distalmost region of elongate shaft 102 and lubricious liner 112. In one embodiment of guide device 14, no portion of radiopaque marker 120 is exposed to bodily fluids. Radiopaque marker 120 may be made of suitable biocompatible materials including, but not limited to, metals, polymers loaded with a radiopaque substance, etc. In one embodiment, radiopaque marker 120 comprises a platinum marker band of a length of 0.040+/−0.003 inches. The platinum marker band has an outer diameter of 0.096+/−0.001 inches and an inner diameter of 0.092+/−0.0005 inches. In the embodiment shown, the outer diameter of the flared distal end of elongate shaft 102 is 0.113+/−0.003 inches and the length of radiopaque marker is 0.04 inches. The length of atraumatic tip 104 ranges from 0.060 to 0.120 inches. The outer rim of atraumatic tip 104 is radiused. The distal end of outer sleeve 106 is tapered as shown and covers part of the protruding distal portion 101 of plastic tube 112. In a preferred embodiment shown, the outer diameter of the distal end of outer sleeve 106 is 0.109+/−0.003 inches.

The distal end of atraumatic tip 104 is designed to be as close to the distal end of radiopaque marker 120 as possible to minimize the length of atraumatic tip 104. In one embodiment of a method of manufacturing guide device 14, a PTFE tube that forms lubricious liner 112 is slid inside elongate shaft 102 made of Nylon. The distal end of elongate shaft 102 is flared to create an annular space between the flared distal end of elongate shaft 102 and lubricious liner 112. Thereafter, a platinum marker band that forms radiopaque marker 120 is slid over the PTFE tube into the annular space between the distal end of elongate shaft 102 and lubricious liner 112. Radiopaque marker 120 is attached to elongate shaft 102 and lubricious liner 112 by a suitable adhesive. Examples of such adhesives include, but are not limited to Loctite™ 4011, etc. A Pebax tube that forms atraumatic tip 104 is slide over lubricious liner 112 such that the Pebax tube abuts against the distal end of elongate shaft 102. A suitable heat shrink tubing is inserted over guide device 14. The distal end of guide device 14 is heated. This fuses the Pebax tube to elongate shaft 102 and also fuses the Pebax tube to lubricious liner 112. Thereafter, the distal end of the Pebax tube may be trimmed. One advantage of this embodiment of a method of manufacturing guide device 14 is a strong bond between elongate shaft 102 made of Nylon and the Pebax tube that forms atraumatic tip 104. Another advantage of this embodiment of a method of manufacturing guide device 14 is that the distal most region of the Pebax tube that forms atraumatic tip 104 may be trimmed as close to the distal end of the platinum marker band to minimize the length of atraumatic tip 104. Such embodiments comprising a short atraumatic tip 104 enable easier navigation and/or torquing and/or repositioning of the distal tip of guide device within the paranasal anatomy with less injury to the patient.

FIG. 5C shows an enlarged view of the proximal portion of the guide device 14 and FIG. 5G shows a cross section through the shaft 102. As shown, in this example the shaft 102 of the guide device 14 comprises an inner liner 111 surrounded by plastic tube 112 which in turn is surrounded by hypotube 114 which in turn is surrounded by outer sleeve 106. In the embodiment shown, hub 108 is attached to the outer surface of outer sleeve 106 by a suitable biocompatible adhesive e.g. Dymax 1191. Hub 108 comprises a hub lumen 118 that is in fluid communication with the lumen enclosed by lubricious liner 112. Hub 118 may be designed such that the transition between hub lumen 118 and the lumen enclosed by lubricious liner 112 is smooth. This allows a seamless transition from hub lumen 118 to the lumen enclosed by lubricious liner 112.

FIG. 5D shows a sectional view of the guide device through the tapered transition portion of the shaft 102 at the distal end of hypotube 114. As shownm, in this example, the distal end of hypotube 114 terminates proximal to the distal end of plastic tube 112 and outer sleeve 106 covers the distal end of the hypotube 114 and tapers to a reduced outer diameter at its distal end, thereby providing a smooth outer surface over the distal end of hypotube 114. In this example, the length of the tapered region of outer cover 106 is 0.20 inches maximum. Thus, in this manner, outer cover 106 creates a smooth transition between the distal end of hypotube 114 and the protruding distal portion 101 of plastic tube 112.

Method and Device for Manufacture of the Guide Catheter

In one embodiment of a method of introducing a curve in elongate shaft 102 of guide device 14, the guide device is gradually bent while a polymeric region of the guide device is heated to a temperature greater than the temperature at which the polymeric region softens. For example, FIGS. 2A and 2B show the steps of a method of introducing an angle or curve in a guide device. FIG. 2A shows a partial sectional view through a bending device 122 comprising a shaping component 124 and a gripping component 126. Shaping component 124 comprises a curved region that defines the final radius of the angled or curved region of guide device 14. In one embodiment, bending device 122 is designed to detachably attach one of multiple shaping components 124 wherein each shaping component 124 has a unique shape. A suitable sized beading 128 is introduced through the lumen of guide device 14 as shown in FIG. 2A. Beading 128 is sized such that the outer diameter of beading 128 is slightly smaller than the diameter of the lumen of guide device 14. In a preferred embodiment, beading 128 is made of PTFE. Thereafter, a heat shrinkable tubing 130 is introduced over guide device 14 and beading 128. Heat shrinkable tubing 130 may be made of suitable polymers including, but not limited to Fluorinated Ethylene-Propylene (FEP), PTFE, PFA, ETFE, MFA, THV, etc. Thereafter, a region of the combination of guide device 14, beading 128 and heat shrinkable tubing 130 is fixed to bending device 122. In the embodiment shown in FIG. 2A, a region of the combination of guide device 14, beading 128 and heat shrinkable tubing 130 is fixed to bending device 122 by a spring grip 132 attached to gripping component 126. A region of guide device 14 to be bent is heated. This region of guide device 14 may be heated by convection or radiation. In one method embodiment, the region of guide device 14 to be bent is heated by blowing hot air on the region of guide device 14 to be bent. The hot air may be generated by a hot box. The temperature of the hot air ranges from 320 to 360 degrees F. In another method embodiment, the region of guide device 14 to be bent is heated by radiant heat generated from an electrical heater. Thereafter, the region of guide device 14 to be bent is bent as shown in FIG. 2B by applying a suitable mechanical bending force. In this embodiment, the region of guide device 14 to be bent was bent after heating the region of guide device 14 to be bent. In an alternate embodiment, the region of guide device 14 to be bent was heated while bending the region of guide device 14 to be bent. After bending the region of guide device 14 to be bent, guide device 14 is cooled. Guide device 14 is removed from bending device 122. Heat shrinkable tubing 130 and beading 128 are removed from guide device 14.

Various design parameters of the guide devices disclosed herein may be defined for quality control of the guide devices. Such parameters may include size parameters, shape parameters, tensile force parameters, etc. In one example, guide device 14 is designed to have a bond of tensile strength of 15 N between hub 108 and outer sleeve 106. In another example guide device 14 is designed to have a bond of tensile strength of 15 N between atraumatic tip 104 and elongate sheath 102. In another example, guide device 14 is designed to withstand a torque of 0.048 N-m applied by torquing hub 108 relative to the straight region of guide device 14 distal to label tubing 110. The applied torque of 0.048 N-m should not cause kinking or failure of the bond between outer sleeve 106 and hypotube 114 or the bond between hub 108 and outer sleeve 106.

Guide device 14 may be used for introducing one or more devices into the anatomy. Examples of such devices include, but are not limited to, over-the-wire balloon catheters, fixed wire balloon catheters, rapid-exchange balloon catheters, guidewires, etc. Guide device 14 may also be used for applying suction to or providing lavage to an anatomical region.

Figure 8:
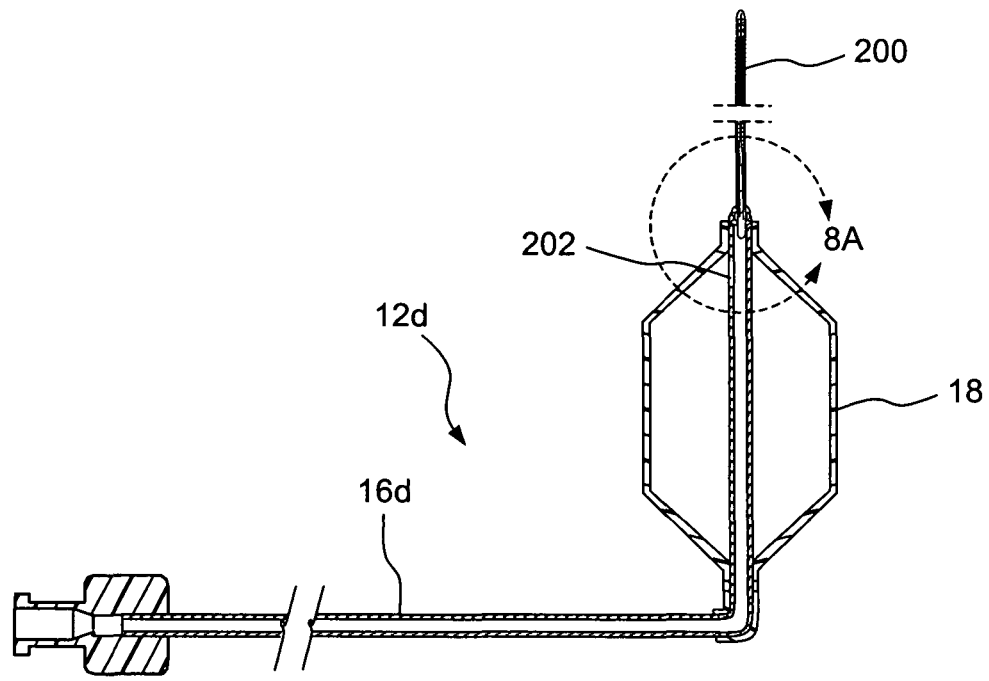
FIG. 8 is a cross sectional view through a longitudinal axis of another embodiment of a non-removable wire balloon catheter, having a curved hypotube shaft.
Figure 8:
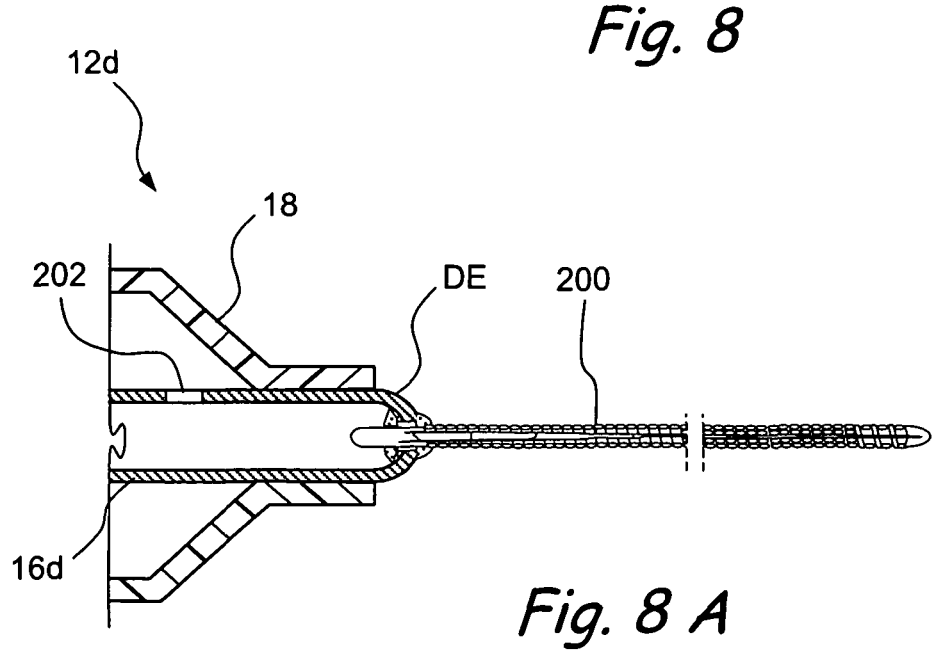
Figure 9:
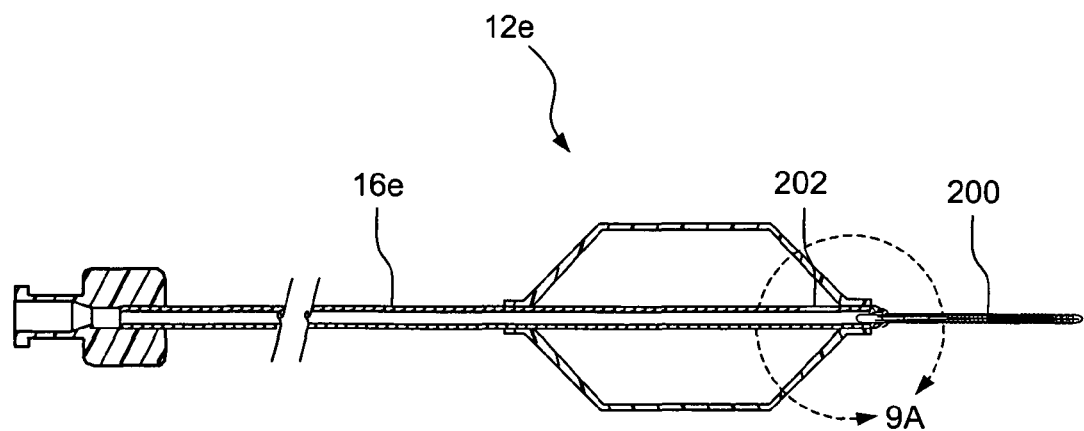
FIG. 9 is a cross sectional view through a longitudinal axis of another embodiment of a non-removable wire balloon catheter, having a straight hypotube shaft.
Figure 9A:
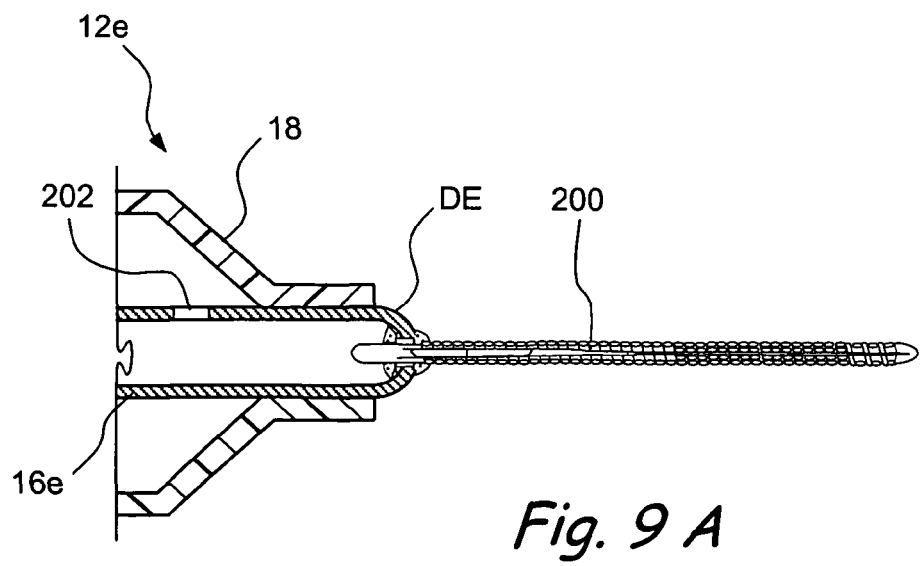
FIG. 9A is an enlarged view of a distal portion of FIG. 9.

It is to be appreciated that the non-removable guide member 22 need not necessarily extend through or into the catheter shaft 16 and the catheter shaft 16 need not necessarily be formed of flexible plastic. For example, FIGS. 8-9A show balloon catheter devices 12d, 12e having a curved tubular metal shaft 16d (FIGS. 8-8A) or a straight tubular metal shaft 16e (FIGS. 9-9A) with a balloon 18 mounted thereon. On opening 202 is formed in the wall of the tubular shaft 16d, 16e to permit inflation fluid to be infused into or extracted from the balloon 18. A non-removable guide member 200 attached to and extendds from the distal end DE of the metal shaft 16d, 16e. In this example, the non-removable guide member 200 does not extend substantially into or through the shaft 16d, 16e as in the embodiments described above. Rather, in this embodiment, the non-removable guide member 200 is attached to and extends distally from the distal end DE of the shaft 16d, 16e, as shown. This non-removable guide member 200 may be attached to the shaft 16d, 16e by soldering, welding, adhesive, threaded connection, crimping of the shaft, frictional engagement, or any other suitable connection technique. Examples of catheters having this type of construction (but lacking the non-removable guide member 22a) include those described in United States Patent Application Publication No. 2004/0064150A1, issued as U.S. Pat. No. 8,317,816 (Becker), the entire disclosure of which is expressly incorporated herein by reference.

Method for Dilating the Ostium of a Maxillary Sinus

FIGS. 7A-7E show steps in one example of a method for using the system 10 of FIG. 1 to dilate the ostium O of a maxillary sinus MS in a human subject. Anatomical structures in FIGS. 7A-7E are labeled as follows:

A number of the drawings in this patent application show anatomical structures of the ear, nose and throat. In general, these anatomical structures are labeled with the following reference letters:

| Nasal Cavity | NC |
|---|---|
| Frontal Sinus | FS |
| Frontal Sinus Ostium | FSO |
| Ethmoid Sinus | ES |
| Sphenoid Sinus | SS |
| Medial Turbinate | MT |
| Maxillary Sinus | MS |
| Uncinate Process | UP |

Figure 7:
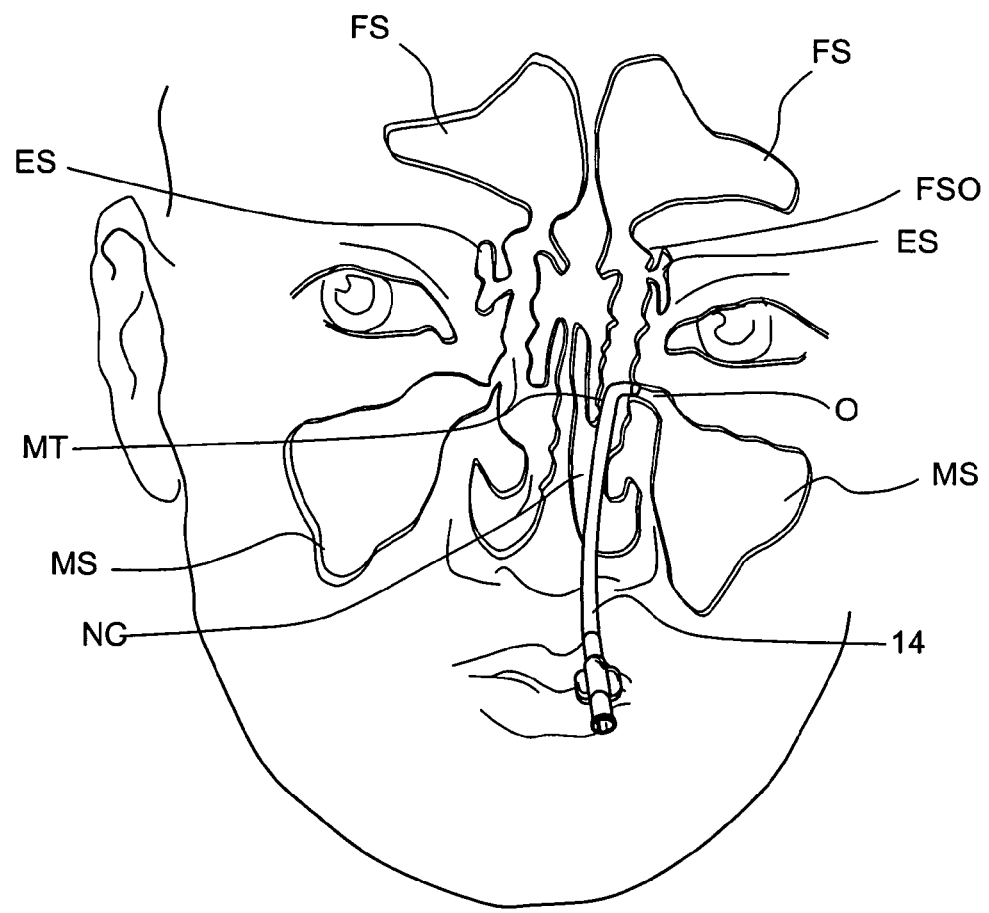
FIGS. 7A-7E show steps in a method for using the system of FIG. 1 to enlarge the ostium of a maxillary sinus in a human subject.

Initially, as shown in FIG. 7A, the guide catheter 14 is inserted trans-nasally, advanced through the nasal cavity NC and positioned such that its distal end is adjacent to the ostium O of the maxillary sinus MS.

Figure 7B:
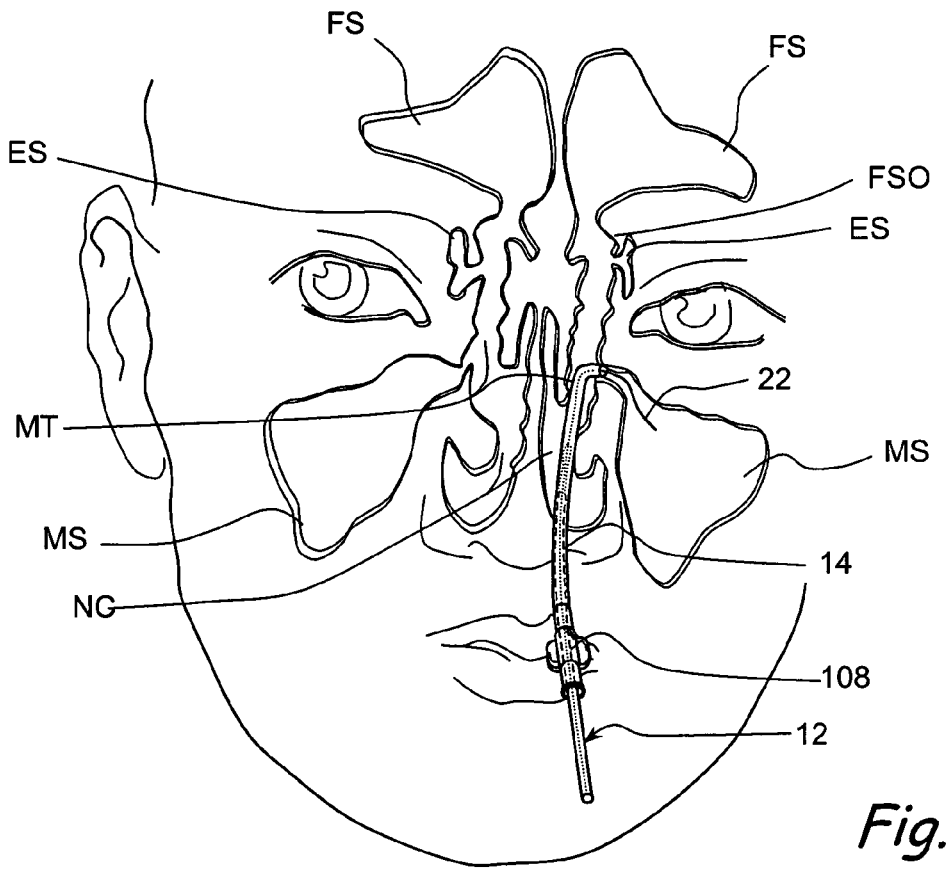

Thereafter, as shown in FIG. 7B, the balloon catheter 12 is inserted through the guide catheter 14 causing the distal portion of the non-removable guide member 22 to pass through the ostium and into the cavity of the maxillary sinus MS.

Figure 7C:
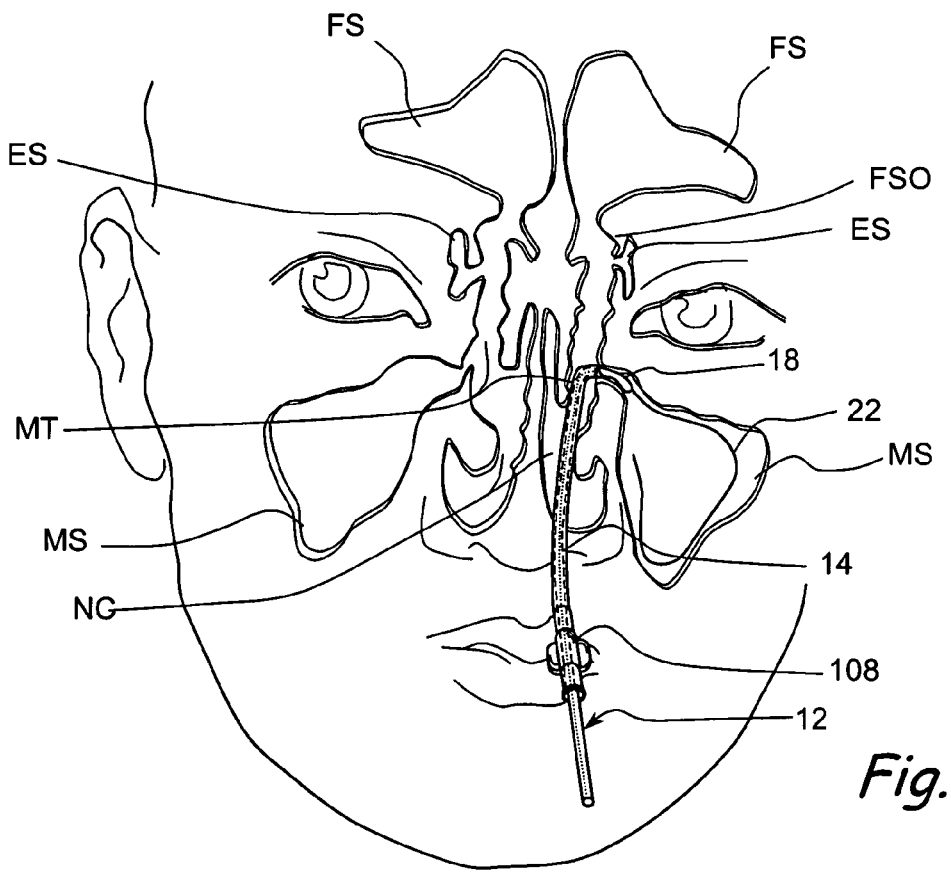

Then, as seen in FIG. 7C, the balloon catheter 14 is further advanced until the entire portion of the non-removable guide member 22 that protrudes beyond the distal end of the catheter shaft 16 is curled within the maxillary sinus MS and the balloon 18 has exited the distal end of the guide catheter 14 and is positioned within the ostium O. The positioning of the balloon within the ostium O may be verified by direct visualization, endoscopically and/or radiographically, as described elsewhere in this patent application.

Figure 7D:
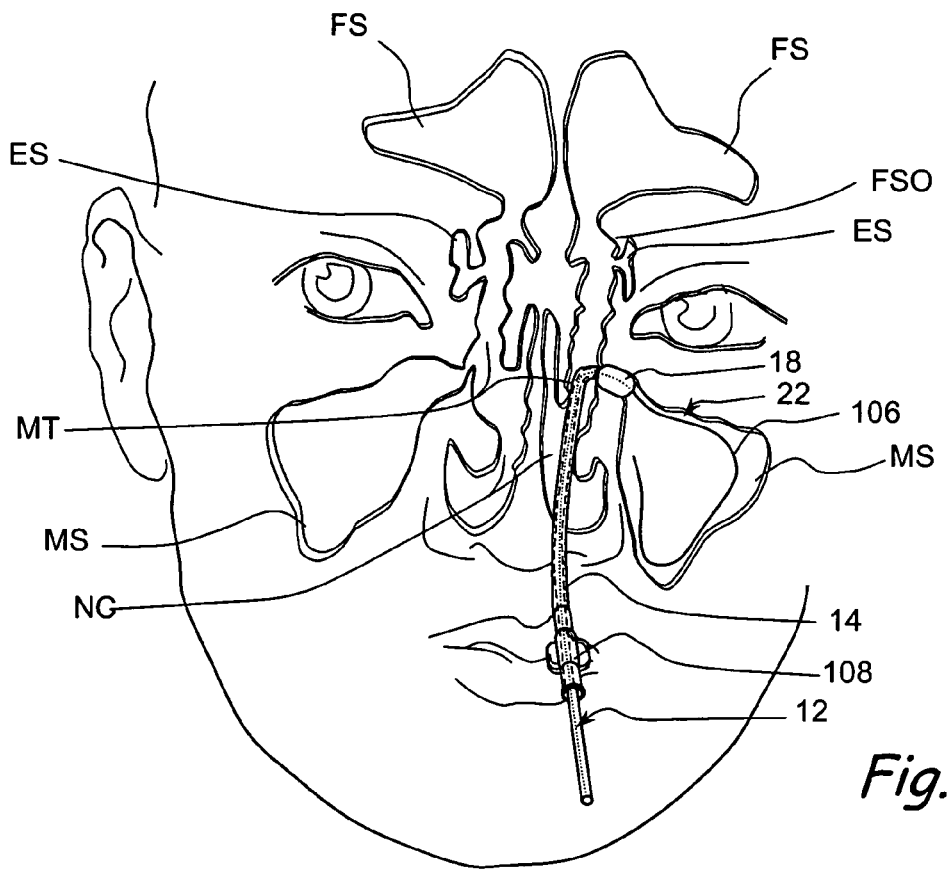

Thereafter, as shown in FIG. 7D, the balloon 18 is inflated one or more times causing the ostium O to dilate.

Figure 7E:
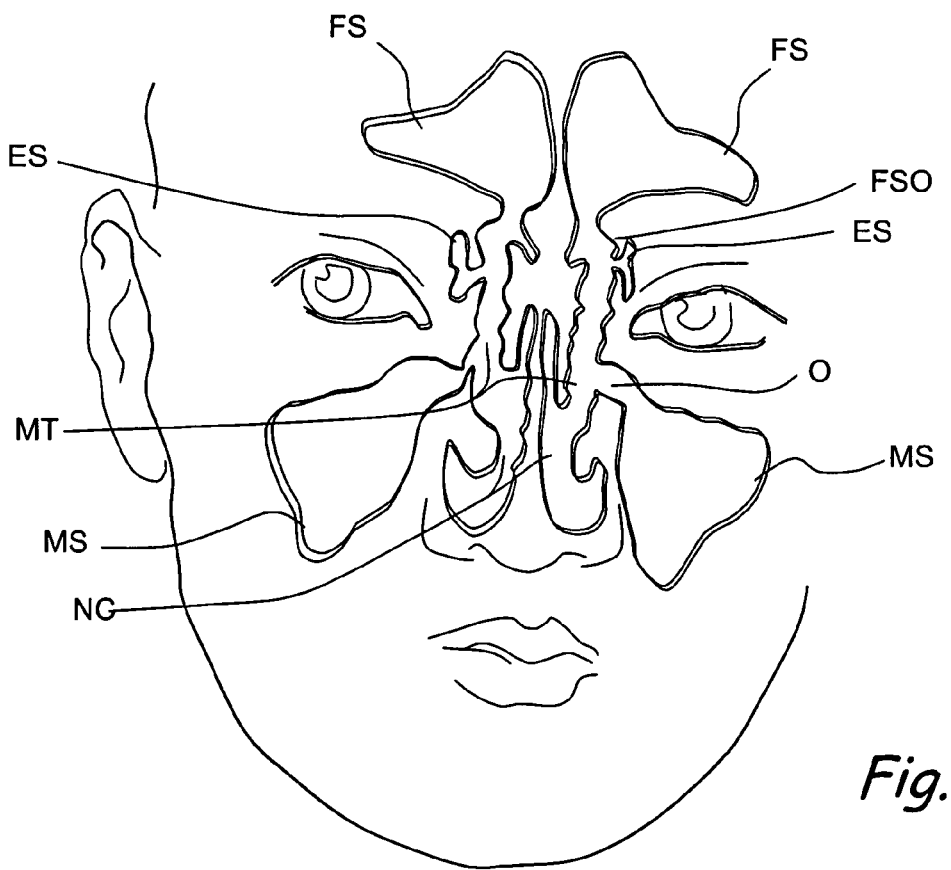

Finally, as shown in FIG. 7E, the balloon is deflated and the balloon catheter 12 and guide catheter 14 are removed. In some cases, the guide catheter 14 may be allowed to remain in place after removal of the balloon catheter 12 and a lavage fluid, other substance or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes and devices that deliver diagnostic or therapeutic agents) may be passed through the guide catheter for further treatment of the condition.

Although the methods and devices disclosed herein are illustrated in conjunction with particular paranasal sinuses, it is understood that these methods and devices can be used in other paranasal sinuses as well as other anatomical passageways of the ear, nose or throat, such as Eustachian tube, larynx, and choana.

Optionally, any of the working devices and guide catheters described herein may be configured or equipped to receive or be advanced over a guidewire or other guide member (e.g., an elongate probe, strand of suture material, other elongate member) unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology. This may include the use of coils, tapered or non-tapered core wires, radiopaque tips and/or entire lengths, shaping ribbons, variations of stiffness, PTFE, silicone, hydrophilic coatings, polymer coatings, etc. For the scope of this invention, these wires may possess dimensions of length between 5 and 75 cm and outer diameter between 0.005" and 0.050".

Several modalities can be used with the devices and methods disclosed herein for navigation and imaging of the devices within the anatomy. For example, the devices disclosed herein may comprise an endoscope for visualization of the target anatomy. The devices may also comprise ultrasound imaging modalities to image the anatomical passageways and other anatomical structures. The devices disclosed herein may comprise one or more magnetic elements especially on the distal end of the devices. Such magnetic elements may be used to navigate through the anatomy by using external magnetic fields. Such navigation may be controlled digitally using a computer interface. The devices disclosed herein may also comprise one or more markers (e.g. infra-red markers). The markers can be used to track the precise position and orientation of the devices using image guidance techniques. Several other imaging or navigating modalities including but not limited to fluoroscopic, radiofrequency localization, electromagnetic, magnetic and other radiative energy based modalities may also be used with the methods and devices disclosed herein. These imaging and navigation technologies may also be referenced by computer directly or indirectly to pre-existing or simultaneously created 3-D or 2-D data sets which help the doctor place the devices within the appropriate region of the anatomy.

It is to be appreciated that the invention has been described herein with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A balloon catheter device for dilating an opening of a paranasal sinus in a human or animal subject, said balloon catheter device comprising:
   a catheter shaft having a proximal end and a distal end; and
   a non-compliant or semi-compliant balloon mounted on the catheter shaft, said balloon being positionable within the opening of the paranasal sinus while in a non-inflated state and thereafter inflatable to an inflated state such that it will cause dilation of the opening of the paranasal sinus;
   at least one position indicating element useable to determine when the balloon is positioned within the opening of the paranasal sinus; and
   non-removable guide member, at least a portion of which extends from the distal end of the catheter shaft, said non-removable guide member having a limited range of axial movement or no movement relative to the catheter shaft, said non-removable guide member being advanceable through the opening of the paranasal sinus ahead of the catheter shaft, at least a distal portion of said non-removable guide member being more flexible in one plane than another;
   wherein the balloon catheter device has a length less than about 20 cm.

2. A catheter device according to claim 1 wherein the non-removable guide member has at least two regions of differing stiffness.

3. A catheter device according to claim 1 wherein a proximal portion of the non-removable guide member resides within the catheter shaft and a distal portion of the guide member extends beyond the distal end of the catheter shaft.

4. A catheter device according to claim 3 wherein the proximal portion of the non-removable guide member extends through the entire length of the catheter shaft.

5. A catheter device according to claim 4 further comprising a hub on the proximal end of the catheter shaft, wherein the proximal portion of the non-removable guide member extends into and is anchored within said hub.

6. A catheter device according to claim 5 wherein the hub comprises a port that is in communication with the balloon to facilitate passage of inflation fluid into and out of the balloon.

7. A catheter device according to claim 6 wherein the hub comprises a fluid infusion port and wherein the crimpable element is crimped in a manner that allows fluid to flow past the location of the crimp.

8. A catheter device according to claim 5 wherein a portion of the hub includes a crimpable element which is crimped so as to engage and hold the proximal portion of the non-removable guide member within the hub.

9. A catheter device according to claim 1 wherein the at least one position indicating element comprises at least one marker on the catheter shaft, said marker being directly or endoscopically visible to the operator when the balloon is positioned within the opening of the paranasal sinus.

10. A catheter device according to claim 1 wherein the at least one position indicating element comprises at least one radiographically visible marker disposed on the non-removable guide member.

11. A catheter device according to claim 10 wherein the non-removable guide member extends through the region of the catheter shaft where the balloon is mounted and wherein radiographic markers are provided on the non-removable guide member to mark the location of the balloon.

12. A catheter device according to claim 11 wherein the balloon has a working length and the non-removable guide member comprises first and second radiographic markers, one of which is at one end of the balloon's working length and the other of which is at the other end of the balloon's working length.

13. A catheter device according to claim 1 wherein the at least one radiographically visible marker comprises a first marker marking the distal end of a working length of the balloon and a second marker marking the proximal end of the working length of the balloon.

14. A catheter device according to claim 1 wherein the balloon is substantially formed of a material selected from the group consisting of: polyethylene terephthalateterephthalate, nylon and polyamide.

15. A catheter device according to claim 1 wherein the balloon is capable of withstanding pressures of more than 22 atmospheres without bursting.

16. A catheter device according to claim 1 or 15 wherein the balloon is capable of breaking bone located around the opening of the paranasal sinus.

17. A catheter device according to claim 16 wherein the balloon is coated with a polymer coating.

18. A catheter device according to claim 16 wherein the coating is dip applied.

19. A catheter device according to claim 1 wherein the balloon is formed substantially of polyethylene terephthalate that is about 0.002 inch thick having a polyurethane coating disposed thereon, said coating being about 0.002 inch thick.

20. A catheter according to claim 1 wherein the balloon is formed substantially of polyethylene terephthalate that is about 0.002 inch thick having a polyurethane coating disposed thereon, said coating being about 0.002 inch thick.

21. A catheter according to claim 1 having a length of less than about 15 cm.

22. A catheter according to claim 1 having a length of less than about 10 cm.

23. A catheter device according to claim 1 wherein the non-removable guide member is formed substantially of a material selected from the group consisting of nickel-titanium alloy and stainless steel.

24. A catheter device according to claim 1 wherein a region of the non-removable guide member adjacent to its distal end comprises a segment of flattened core wire surrounded by a helical wire coil.

25. A catheter device according to claim 24 wherein the segment of flattened core wire has a height of from about 0.001 inch to about 0.004 inch.

26. A catheter device according to claim 1 wherein the non-removable guide member comprises a wire core having a proximal portion, a middle portion and a distal portion, said proximal portion being of substantially uniform diameter, said middle portion that is smaller in diameter at its distal end than at its proximal end and a distal portion of substantially uniform diameter.

27. A catheter device according to claim 26 wherein the proximal portion of the core wire has a diameter of 0.025 +/−0.0005 inch.

28. A catheter device according to claim 26 wherein the distal portion of the core wire is flattened.

29. A catheter device according to claim 26 or 28 wherein a helical wire coil surrounds the distal portion and at least some of the middle portion of the core wire.

30. A catheter device according to claim 29 wherein the helical wire coil has an outer diameter of from about 0.014 inch to about 0.038 inch.

31. A catheter device according to claim 28 wherein the flattened distal portion of the core wire has a flattened thickness of 0.001 to 0.006 inches.

32. A catheter device according to claim 1 wherein the non-removable guide member has a substantially radiolucent proximal region, a radiopaque middle region and a substantially radiolucent distal region.

33. A catheter device according to claim 32 wherein said at least one position indicating element comprises the radiopaque middle region of the non-removable guide member.

34. A catheter device according to claim 33 wherein the balloon has a working length and the position of the radiopaque middle region is coterminus with the working length of the balloon.

35. A catheter device according to claim 1 wherein at least a portion of the non-removable guide member extending beyond the distal end of the catheter shaft may be trimmed.

36. A catheter device according to claim 1 wherein the non-removable guide member is secured to the catheter device by adhesive.

37. A catheter device according to claim 1 wherein an outer polymer covering is disposed on at least a portion of the catheter device.

38. A catheter device according to claim 37 wherein the outer covering comprises heat-shrinkable material.

39. A catheter device according to claim 38 wherein the heat shrinkable material comprises polyether block amide.

40. A catheter device according to claim 1 wherein the balloon has a working length of about 12 to about 24 mm.

41. A system comprising a balloon catheter device according to claim 1 in combination with a guide catheter having a lumen through which the balloon catheter device is insertable.

42. A system according to claim 41 wherein the guide catheter has a substantially non-removable shape.

43. A system according to claim 42 wherein the guide catheter has a curve of between 0 degrees to about 135 degrees.

44. A system according to claim 42 further comprising a tubular outer cover having a distal end.

45. A system according to claim 44 wherein the outer cover extends beyond the distal end of the metal tube but terminates short of the distal end of the plastic tube.

46. A system according to claim 45 wherein the outer cover has a distal end that is tapered so as to provide a smooth transition from the outer surface of the plastic tube.

47. A system according to claim 42 or 44 further comprising an inner liner lining the lumen of the plastic tube.

48. A system according to claim 47 wherein a radiopaque marker is captured between the inner liner and the plastic tube.

49. A system according to claim 48 wherein the distal end of the plastic tube stops short of the distal end of the inner liner such that a distal portion of the inner liner protrudes beyond the distal end of the plastic tube, and wherein an atraumatic tip member formed of material that is softer than the plastic tube is disposed about the distal portion of the inner liner.

50. A system according to claim 41 wherein the guide catheter comprises a metal tube having a lumen and a distal end and a plastic tube having a lumen and a distal end, said plastic tube extending coaxially through the lumen of the metal tube with a distal portion of the plastic tube extending out of and beyond the distal end of the metal tube.

51. A system according to claim 50 wherein the distal portion of the plastic tube is curved.

52. A catheter device according to claim 1 wherein the distal portion of the non-removable guide member that extends beyond the end of the catheter shaft is an atraumatic tip.

53. A catheter device according to claim 1 wherein at least a portion of the non-removable guide member is coated.

54. A catheter device according to claim 1 wherein the balloon is coated with a polymer coating and at least a portion of the non-removable guide member is coated with a different coating.

55. A catheter device according to claim 1 wherein the catheter shaft is flexible.

56. A catheter device according to claim 1 wherein the catheter shaft is formed of plastic.

57. A catheter device according to claim 1 wherein the catheter shaft is formed of metal.

58. A catheter device according to claim 57 wherein the catheter shaft is formed of metal hypotube.

59. A catheter device according to claim 57 wherein the catheter shaft is formed of straight metal tube.

60. A catheter device according to claim 57 wherein the catheter shaft is formed of curved metal tube.

* * * * *